US011388871B2

(12) United States Patent
Andrés et al.

(10) Patent No.: US 11,388,871 B2
(45) Date of Patent: Jul. 19, 2022

(54) MELON PLANTS WITH IMPROVED DISEASE RESISTANCE

(71) Applicant: SEMINIS VEGETABLE SEEDS, INC., St. Louis, MO (US)

(72) Inventors: Susana García Andrés, Almeria (ES); Maria Dolores Hernandez, Roldán (ES); Robyn L. Morgan, Fredericton, CA (US)

(73) Assignee: SEMINIS VEGETABLE SEEDS, INC, St. Louis, MO (US)

( * ) Notice: Subject to any disclaimer, the term of this patent is extended or adjusted under 35 U.S.C. 154(b) by 117 days.

(21) Appl. No.: 16/636,627

(22) PCT Filed: Aug. 6, 2018

(86) PCT No.: PCT/US2018/045321
§ 371 (c)(1),
(2) Date: Feb. 4, 2020

(87) PCT Pub. No.: WO2019/032427
PCT Pub. Date: Feb. 14, 2019

(65) Prior Publication Data

US 2021/0054401 A1 Feb. 25, 2021

Related U.S. Application Data

(60) Provisional application No. 62/542,722, filed on Aug. 8, 2017.

(51) Int. Cl.

| | |
|---|---|
| ***C12Q 1/6827*** | (2018.01) |
| ***A01H 6/34*** | (2018.01) |
| ***C12N 15/82*** | (2006.01) |
| ***C12Q 1/6869*** | (2018.01) |
| ***C12Q 1/6895*** | (2018.01) |

(52) U.S. Cl.
CPC ......... *A01H 6/344* (2018.05); *C12N 15/8283* (2013.01); *C12Q 1/6827* (2013.01); *C12Q 1/6869* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2019/0225983 A1 7/2019 Lizarzaburu Chavez et al.
2020/0040355 A1* 2/2020 Lizarzaburu Chavez .................. C12N 15/8283

FOREIGN PATENT DOCUMENTS

| | | |
|---|---|---|
| WO | 2014/031770 | 2/2014 |
| WO | WO 2017/114848 | 7/2017 |
| WO | WO 2018/011075 | 1/2018 |
| WO | 2018/219861 | 12/2018 |

OTHER PUBLICATIONS

Romay, et al. (Plant disease 103.11 (2019): 2913-2919) (Year: 2019).*
Lopez et al., "Mechanical transmission of Tomato leaf curl New Delhi virus to cucurbit germplasm: selection of tolerance sources in Cucumis melo," Euphytica, 2015, 204, 679-691.
Saez et al., "Inheritance of Tolerance to Tomato Leaf Curl New Delhi Virus (ToLCNDV) in Melon," Cucurbitaceae 2016, XIth Eucarpia Meeting on Cucurbit Genetics & Breeding, Warsaw, Poland, 2016, pp. 214-216, ref.9.
GenBank LN681848, "Cucumis melo genomic scaffold, anchoredscaffold00006," retrieved from the internet https://www.ncbi.nlm.nih.gov/nuccorG/LN681848; 2015.
PCT International Search Report for PCT/US 2018/45321; dated Dec. 4, 2018.
PCT Written Opinion of the International Searching Authority for PCT/US 2018/45321; dated Dec. 4, 2018.
Saez et al. "Resistance to tomato leaf curl New Delhi virus in melon is controlled by a major QTL located in chromosome 11 " Plant Cell Rep; vol. 36, No. 10, pp. 1571-1584; 2017.
Extended European Search Report regarding European Application No. 18844387.3, dated May 3, 2021.

* cited by examiner

*Primary Examiner* — Charles Logsdon
(74) *Attorney, Agent, or Firm* — Dentons US LLP; Matthew Madsen

(57) ABSTRACT

Melon plants exhibiting resistance to Tomato leaf curl New Delhi virus (ToLCNDV) are provided, together with methods of producing, identifying, or selecting plants or germplasm with a ToLCNDV resistance phenotype. Such plants include melon plants comprising introgressed genomic regions conferring disease resistance. Compositions, including novel polymorphic markers for detecting plants comprising introgressed disease resistance alleles, are further provided.

20 Claims, No Drawings

Specification includes a Sequence Listing.

MELON PLANTS WITH IMPROVED DISEASE RESISTANCE

REFERENCE TO RELATED APPLICATION

This application is a 371 National Stage application of International Application No. PCT/US18/45321, filed Aug. 6, 2018, which claims the benefit of U.S. Provisional Application No. 62/542,722, filed on Aug. 8, 2017, which is incorporated herein by reference in their entireties.

INCORPORATION OF SEQUENCE LISTING

A sequence listing containing the file named "SEMB028WO_ST25.txt" which is 46.4 bytes (measured in MS-Windows®) and created on Jul. 30, 2018, and comprises 110 sequences, and is incorporated herein by reference in its entirety.

FIELD OF THE INVENTION

The present invention relates to the field of plant breeding and more specifically to methods and compositions for producing melon plants exhibiting improved disease resistance.

BACKGROUND

Disease resistance is an important trait in agriculture, particularly for the production of food crops. A severe outbreak of Tomato leaf curl New Delhi virus (ToLCNDV) occurred in squash and melons in the main production area of southern Spain in 2012-2014. This virus is becoming an increasingly significant cause of yield loss and even plant death in melon plants. As ToLCNDV-resistant commercial varieties of melon are not currently available, reduction of crop damage is typically accomplished through the establishment of integrated control measures to reduce the spread of virus via whiteflies. Therefore, it is necessary that breeders find and develop sources of ToLCNDV resistance to minimize crop loss in commercial melon production.

SUMMARY

In one aspect, the invention provides an elite *Cucumis melo* plant comprising a first introgressed allele on a first chromosome selected from the group consisting of chromosomes 6, 11, 2, and 12, wherein said first introgressed allele confers to a plant increased resistance to Tomato leaf curl New Delhi virus (ToLCNDV) compared to a plant not comprising said allele. In certain embodiments, said plant further comprises a second introgressed allele on a second chromosome selected from the group consisting of chromosomes 6, 11, 2, and 12, wherein said second introgressed allele confers to a plant increased resistance to Tomato leaf curl New Delhi virus (ToLCNDV) compared to a plant not comprising said allele. Said plant may further comprise a third introgressed allele on a third chromosome selected from the group consisting of chromosomes 6, 11, 2, and 12, wherein said third introgressed allele confers to a plant increased resistance to Tomato leaf curl New Delhi virus (ToLCNDV) compared to a plant not comprising said allele. In yet further embodiments, said plant further comprises a fourth introgressed allele on a fourth chromosome selected from the group consisting of chromosomes 6, 11, 2, and 12, wherein said fourth introgressed allele confers to a plant increased resistance to Tomato leaf curl New Delhi virus (ToLCNDV) compared to a plant not comprising said allele. In some embodiments, said first introgressed allele is introgressed from a *Cucumis melo* ssp *agrestis* plant. Said first introgressed allele may further comprise the resistance haplotype of PI414723.

In certain embodiments, the invention provides plants comprising introgressed alleles flanked in the genome of said plant by: a) marker locus Marker_1 (SEQ ID NO: 1) and marker locus Marker_5 (SEQ ID NO: 21) on chromosome 2; b) marker locus Marker_9 (SEQ ID NO: 26) and marker locus Marker_13 (SEQ ID NO: 46) on chromosome 6; c) marker locus Marker_17 (SEQ ID NO: 51) and marker locus Marker_21 (SEQ ID NO: 71) on chromosome 11; or d) marker locus Marker_25 (SEQ ID NO: 76) and marker locus Marker_27 (SEQ ID NO: 86) on chromosome 12. For example, in some embodiments, said first introgressed allele is flanked in the genome of said plant by marker locus Marker_1 (SEQ ID NO: 1) and marker locus Marker_5 (SEQ ID NO: 21) on chromosome 2. In other embodiments, said first introgressed allele is flanked in the genome of said plant by marker locus Marker_9 (SEQ ID NO: 26) and marker locus Marker_13 (SEQ ID NO: 46) on chromosome 6. In further embodiments, said first introgressed allele is flanked in the genome of said plant by marker locus Marker_9 (SEQ ID NO: 26) and marker locus Marker_29 (SEQ ID NO: 91) on chromosome 6. In some embodiments, said first introgressed allele is flanked in the genome of said plant by marker locus Marker_17 (SEQ ID NO: 51) and marker locus Marker_21 (SEQ ID NO: 71) on chromosome 11. In further embodiments, said first introgressed allele is flanked in the genome of said plant by marker locus Marker_30 (SEQ ID NO: 96) and marker locus Marker_32 (SEQ ID NO: 106) on chromosome 11. In still further embodiments, said first introgressed allele is flanked in the genome of said plant by marker locus Marker_25 (SEQ ID NO: 76) and marker locus Marker_27 (SEQ ID NO: 86) on chromosome 12. The invention further provides a plant part of a plant provided herein, for example a cell, a seed, a root, a stem, a leaf, a fruit, a flower, or pollen.

In another aspect, the invention provides methods of selecting a *Cucumis melo* plant exhibiting resistance ToLCNDV, comprising: a) crossing the *Cucumis melo* plant provided herein with itself or with a second *Cucumis melo* plant of a different genotype to produce one or more progeny plants; and b) selecting a progeny plant comprising a first introgressed allele. In certain embodiments, selecting said progeny plant comprises identifying a genetic marker genetically linked to said first introgressed allele. In some embodiments, selecting a progeny plant comprises: a) identifying a genetic marker within or genetically linked to a genomic region between marker locus Marker_1 (SEQ ID NO: 1) and marker locus Marker_5 (SEQ ID NO: 21) on chromosome 2; b) identifying a genetic marker within or genetically linked to a genomic region between marker locus Marker_9 (SEQ ID NO: 26) and marker locus Marker_13 (SEQ ID NO: 46) on chromosome 6; c) identifying a genetic marker within or genetically linked to a genomic region between marker locus Marker_17 (SEQ ID NO: 51) and marker locus Marker_21 (SEQ ID NO: 71) on chromosome 11; or d) identifying a genetic marker within or genetically linked to a genomic region between marker locus Marker_25 (SEQ ID NO: 76) and marker locus Marker_27 (SEQ ID NO: 86) on chromosome 12. In other embodiments, selecting a progeny plant comprises identifying a genetic marker within or genetically linked to a genomic region between marker locus Marker_9 (SEQ ID NO: 26) and marker locus Marker_29 (SEQ ID NO: 91) on chromosome 6. In some embodiments, selecting a progeny plant comprises identifying a genetic marker within or genetically linked to a genomic region between marker locus Marker_30 (SEQ ID NO: 96) and marker locus Marker_32 (SEQ ID NO: 106) on chromosome 11.

In other embodiments, selecting a progeny plant comprises: a) identifying a genetic marker within or genetically linked to a genomic region between marker locus Marker_1 (SEQ ID NO: 1) and marker locus Marker_5 (SEQ ID NO: 21) on chromosome 2; and b) identifying a genetic marker within or genetically linked to a genomic region between marker locus Marker_17 (SEQ ID NO: 51) and marker locus Marker_21 (SEQ ID NO: 71) on chromosome 11. In further embodiments, selecting a progeny plant comprises: a) identifying a genetic marker within or genetically linked to a genomic region between marker locus Marker_1 (SEQ ID NO: 1) and marker locus Marker_5 (SEQ ID NO: 21) on chromosome 2; and b) identifying a genetic marker within or genetically linked to a genomic region between marker locus Marker_30 (SEQ ID NO: 96) and marker locus Marker_32 (SEQ ID NO: 106) on chromosome 11. In yet further embodiments, selecting a progeny plant further comprises detecting at least one polymorphism at a locus selected from the group consisting of marker locus Marker_2 (SEQ ID NO: 6), marker locus Marker_3 (SEQ ID NO: 11), marker locus Marker_4 (SEQ ID NO: 16), marker locus Marker_18 (SEQ ID NO: 56), marker locus Marker_19 (SEQ ID NO: 61), marker locus Marker_20 (SEQ ID NO: 66), and marker locus Marker_31 (SEQ ID NO: 101). For example, in some embodiments, selecting a progeny plant comprises identifying a genetic marker within or genetically linked to a genomic region between marker locus Marker_9 (SEQ ID NO: 26) and marker locus Marker_13 (SEQ ID NO: 46) on chromosome 6. In other embodiments, selecting a progeny plant comprises identifying a genetic marker within or genetically linked to a genomic region between marker locus Marker_9 (SEQ ID NO: 26) and marker locus Marker_29 (SEQ ID NO: 91) on chromosome 6. In further embodiments, selecting a progeny plant further comprises detecting at least one polymorphism at a locus selected from the group consisting of marker locus Marker_10 (SEQ ID NO: 31), marker locus Marker_11 (SEQ ID NO: 36), and marker locus Marker_12 (SEQ ID NO: 41). In yet further embodiments, selecting a progeny plant comprises identifying a genetic marker within or genetically linked to a genomic region between marker locus Marker_25 (SEQ ID NO: 76) and marker locus Marker_27 (SEQ ID NO: 86) on chromosome 12. In still further embodiments, selecting a progeny plant further comprises detecting at least one polymorphism at marker locus Marker_26 (SEQ ID NO: 81). The invention further provides embodiments wherein said progeny plant is an $F_2$-$F_6$ progeny plant, wherein producing said progeny plant comprises backcrossing, and wherein backcrossing comprises from 2-7 generations of backcrossing.

In another aspect, the invention provides a method of producing a *Cucumis melo* plant exhibiting resistance to ToLCNDV, comprising introgressing into a plant a ToLCNDV resistance allele, wherein said resistance allele is defined as located in a genomic region between: a) marker locus Marker_1 (SEQ ID NO: 1) and marker locus Marker_5 (SEQ ID NO: 21) on chromosome 2; b) marker locus Marker_9 (SEQ ID NO: 26) and marker locus Marker_13 (SEQ ID NO: 46) on chromosome 6; c) marker locus Marker_17 (SEQ ID NO: 51) and marker locus Marker_21 (SEQ ID NO: 71) on chromosome 11; or d) marker locus Marker_25 (SEQ ID NO: 76) and marker locus Marker_27 (SEQ ID NO: 86) on chromosome 12. In some embodiments, a method of producing a *Cucumis melo* plant exhibiting resistance to ToLCNDV, comprising introgressing into a plant a ToLCNDV resistance allele, wherein said resistance allele is defined as located in a genomic region between marker locus Marker_9 (SEQ ID NO: 26) and marker locus Marker_29 (SEQ ID NO: 91) on chromosome 6 is provided herein. In other embodiments, a method of producing a *Cucumis melo* plant exhibiting resistance to ToLCNDV, comprising introgressing into a plant a ToLCNDV resistance allele, wherein said resistance allele is defined as located in a genomic region between marker locus Marker_30 (SEQ ID NO: 96) and marker locus Marker_32 (SEQ ID NO: 106) on chromosome 11 is provided herein. In some embodiments, introgressing comprises backcrossing or marker-assisted selection. In further embodiments, introgressing comprises detecting at least one polymorphism at a locus selected from the group consisting of marker locus Marker_1 (SEQ ID NO: 1), marker locus Marker_2 (SEQ ID NO: 6), marker locus Marker_3 (SEQ ID NO: 11), marker locus Marker_4 (SEQ ID NO: 16), marker locus Marker_5 (SEQ ID NO: 21), marker locus Marker_9 (SEQ ID NO: 26), marker locus Marker_10 (SEQ ID NO: 31), marker locus Marker_11 (SEQ ID NO: 36), marker locus Marker_12 (SEQ ID NO: 41), marker locus Marker_13 (SEQ ID NO: 46), marker locus Marker_17 (SEQ ID NO: 51), marker locus Marker_18 (SEQ ID NO: 56), marker locus Marker_19 (SEQ ID NO: 61), marker locus Marker_20 (SEQ ID NO: 66), marker locus Marker_21 (SEQ ID NO: 71), marker locus Marker_25 (SEQ ID NO: 76), marker locus Marker_26 (SEQ ID NO: 81), marker locus Marker_27 (SEQ ID NO: 86), marker locus Marker_29 (SEQ ID NO: 91), marker locus Marker_30 (SEQ ID NO: 96), marker locus Marker_31 (SEQ ID NO: 101), and marker locus Marker_32 (SEQ ID NO: 106). The invention further provides *Cucumis melo* plants obtainable by the methods provided herein.

DETAILED DESCRIPTION

The new outbreak of Tomato leaf curl New Delhi virus (ToLCNDV) has become responsible for severe crop losses in cucurbits in the past several years. Initially, ToLCNDV was most damaging to zucchini crops, but recently losses of melon have been very high in both intensive production areas of southeastern Spain and traditional open field cultivation areas of central Spain. In certain open field cultivation settings, the virus affects up to 80% of the late melon crop. ToLCNDV is spread by whitefly and is considered a serious threat to greenhouse and open-field melon production.

Commercial melon varieties having ToLCNDV resistance have not previously been available, and therefore efforts to reduce crop damage have been focused on the establishment of integrated control measures for reducing the source or spread of infection. Although sources of ToLCNDV resistance exist, quantitative trait loci (QTLs) controlling ToLCNDV resistance have not previously been identified and it has not been possible to produce elite plants for commercial use comprising the resistance. As resistance against ToLCNDV is becoming more important due to its aggressiveness and rapid emergence as a primary disease in melon plants, methods of producing, detecting and tracking resistant plants using genetic markers for ToLCNDV resistance are needed.

The invention therefore provides novel ToLCNDV resistance loci on chromosomes 6, 11, 2, and 12 of the *Cucumis melo* genome. A first major quantitative trait locus (QTL) has been identified within a 22 cM chromosomal segment on chromosome 6 flanked by marker locus Marker_9 (SEQ ID NO: 26) and marker locus Marker_13 (SEQ ID NO: 46). In another embodiment of the invention, the QTL on chromosome 6 is a 10 cM chromosomal segment flanked by marker locus Marker_9 and marker locus Marker_29 (SEQ ID NO: 91). Marker_9 is a SNP change [T/C] at 2,970,811 bp of the public melon genome map 3.5.1 (Argyris, et al. *BMC Genomics* 2015; 16:4; publically available on the internet through the Melonomics network, or at the cucurbits genomics database), while Marker_13 is a SNP change [A/G] at 874,401 bp. Marker_10 (SEQ ID NO: 31), a SNP change [T/G] at 2,296,368 bp, Marker_11 (SEQ ID NO: 36), a SNP change [T/C] at 1,500,067 bp, Marker_12 (SEQ ID NO: 41), a SNP change [C/G] at 1,162,868 bp, and Marker_29 (SEQ ID NO: 91), a SNP change [C/T] at 1,887,147 bp, are located between Marker_9 and Marker_13 and can be used, in addition to the flanking markers to select for the ToLCNDV resistance locus on chromosome 6.

A second major ToLCNDV resistance QTL has been identified within a 5.2 cM chromosomal segment on chromosome 11 flanked by marker locus Marker_30 (SEQ ID NO: 96) and marker locus Marker_32 (SEQ ID NO: 106). Marker_30 is a SNP change [C/T] at 30,131,582 bp of the public melon genome map 3.5.1 and Marker_32 is a SNP change [A/G] at 29,515,226 bp. Interstitial markers, such as Marker_18 (SEQ ID NO: 56), a SNP change [T/C] at 29,787,219 bp, Marker_19 (SEQ ID NO: 61), a SNP change [T/C] at 29,728,032 bp, and Marker_31 (SEQ ID NO: 101), a SNP change [A/C] at 29,809,231 bp, can be used in addition to the flanking markers to select for the locus on chromosome 11.

A further QTL on chromosome 2 has been identified within a 15 cM interval located between Marker_1 (SEQ ID NO: 1), a SNP change [A/G] at 573,028 bp of the public melon genome map 3.5.1 and Marker_5 (SEQ ID NO: 21), a SNP change [A/G] at 1,581,938 bp. Interstitial markers, such as Marker_2 (SEQ ID NO: 6), a SNP change [A/C] at 644,655 bp, Marker_3 (SEQ ID NO: 11), a SNP change [T/C] at 801,778 bp, and Marker_4 (SEQ ID NO: 16), a SNP change [T/G] at 1,037,024 bp, can be used in addition to the flanking markers to select for the ToLCNDV resistance locus on chromosome 2.

An additional QTL on chromosome 12 has been identified within a 30 cM interval located between Marker_25 (SEQ ID NO: 76), a SNP change [T/C] at 3,541,677 bp of the public melon genome map 3.5.1 and Marker_27 (SEQ ID NO: 86), a SNP change [A/C] at 20,605,436 bp. In addition to the flanking markers, Marker_26 (SEQ ID NO: 81), a SNP change [A/T] at 15,323,352 bp can be used to select for the resistance QTL on chromosome 12.

The invention further provides melon plants comprising introgressed ToLCNDV resistance alleles at one, two, three, or all of the newly identified resistance loci provided herein. For example, a plant provided herein may comprise an introgressed ToLCNDV resistance allele within a chromosomal segment flanked by marker locus Marker_9 and marker locus Marker_13 on chromosome 6 or within a chromosomal segment flanked by marker locus Marker_30 and marker locus Marker_32 on chromosome 11. In another embodiment, a plant of the invention may comprise introgressed ToLCNDV resistance alleles within a chromosomal segment flanked by marker locus Marker_9 and marker locus Marker_13 on chromosome 6 and also within a chromosomal segment flanked by marker locus Marker_17 and marker locus Marker_21 on chromosome 11. Plants of the invention may comprise introgressed ToLCNDV resistance alleles at any one, two, three, or four of the resistance loci disclosed herein.

Novel trait-linked markers are further provided that allow the accurate identification and tracking of the chromosomal regions provided herein during plant breeding. In particular embodiments, the invention provides genetic markers within or genetically linked to the chromosomal segments provided herein. Other embodiments provide novel markers Marker_1 (SEQ ID NO: 1), marker locus Marker_2 (SEQ ID NO: 6), marker locus Marker_3 (SEQ ID NO: 11), marker locus Marker_4 (SEQ ID NO: 16), marker locus Marker_5 (SEQ ID NO: 21), marker locus Marker_9 (SEQ ID NO: 26), marker locus Marker_10 (SEQ ID NO: 31), marker locus Marker_11 (SEQ ID NO: 36), marker locus Marker_12 (SEQ ID NO: 41), marker locus Marker_13 (SEQ ID NO: 46), marker locus Marker_17 (SEQ ID NO: 51), marker locus Marker_18 (SEQ ID NO: 56), marker locus Marker_19 (SEQ ID NO: 61), marker locus Marker_20 (SEQ ID NO: 66), marker locus Marker_21 (SEQ ID NO: 71), marker locus Marker_25 (SEQ ID NO: 76), marker locus Marker_26 (SEQ ID NO: 81), marker locus Marker_27 (SEQ ID NO: 86), marker locus Marker_29 (SEQ ID NO: 91), marker locus Marker_30 (SEQ ID NO: 96), marker locus Marker_31 (SEQ ID NO: 101), and marker locus Marker_32 (SEQ ID NO: 106), which are useful in detection and tracking of plants comprising ToLCNDV resistance.

I. Genomic Regions, Alleles, and Polymorphisms Associated with ToLCNDV Resistance in Melon Plants Donors for resistance to ToLCNDV have been identified among wild or uncultivated melon lines, including PI414723, WM7, WM9, IC-274014, PI124112 and PI282448, and a single resistance region has been identified when mapping the resistance of WM7. Using the newly identified resistance loci identified herein, resistance from any source can be introgressed into an elite line using the methods and genetic markers provided herein. In certain examples, resistance may be introgressed from PI414723, a *Cucumis melo* ssp *agrestis* wild-type line.

In certain embodiments, the invention therefore provides melon plants comprising donor DNA from a ToLCNDV resistant line that maps between Marker_9 and Marker_13 on chromosome 6, between Marker_30 and Marker_32 on chromosome 11, between Marker_1 and Marker_5 on chromosome 2, or between Marker_25 and Marker_27 on chromosome 12. Genomic regions as described herein can be obtained from any wild or cultivated plant or line, including in certain embodiments melon line PI414723, available at the USDA National Plant Germplasm System. Plants provided herein include plants comprising the genetic source for the ToLCNDV resistance trait from melon line PI414723. In certain embodiments, the locus on chromosome 6 conferring ToLCNDV resistance is between Marker_9 and Marker_29. In another embodiment, the locus on chromosome 11 conferring ToLCNDV resistance is between Marker_17 and Marker_21.

II. Introgression of Genomic Regions Associated with ToLCNDV Resistance

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel markers for identifying and tracking introgression of one or more of the genomic regions disclosed herein from a ToLCNDV resistant plant into a cultivated line. The invention further provides markers for identifying and tracking the novel introgressions disclosed herein during plant breeding, such as marker locus Marker_1, marker locus Marker_2, marker locus Marker_3, marker locus Marker_4, marker locus Marker_5, marker locus Marker_9, marker locus Marker_10, marker locus Marker_11, marker locus Marker_12, marker locus Marker_13, marker locus Marker_17, marker locus Marker 18, marker locus Marker_19, marker locus Marker_20, marker locus Marker_21, marker locus Marker_25, marker locus Marker_26, marker locus Marker_27, marker locus Marker_29, marker locus Marker_30, marker locus Marker_31, and marker locus Marker_32, which are useful in detection and tracking of plants comprising ToLCNDV resistance.

Markers within or linked to any of the genomic intervals of the present invention may be useful in a variety of breeding efforts that include introgression of genomic regions associated with disease resistance into a desired genetic background. For example, a marker within 40 cM, 20 cM, 15 cM, 10 cM, 5 cM, 2 cM, or 1 cM of a marker associated with disease resistance described herein can be used for marker-assisted introgression of genomic regions associated with a disease resistance phenotype.

Melon plants comprising one or more introgressed regions associated with a desired phenotype wherein at least 10%, 25%, 50%, 75%, 90%, or 99% of the remaining genomic sequences carry markers whose alleles match the recurrent parent genotype outside of the region targeted for disease resistance introgression are also provided. Melon plants comprising an introgressed region closely linked to, or adjacent to, the genomic regions and markers provided herein and associated with a disease resistance phenotype are also provided.

III. Development of ToLCNDV Resistant Melon Varieties

For most breeding objectives, commercial breeders work within germplasm that is "cultivated," "cultivated type," or "elite." As used herein, "elite" or "cultivated" variety means a variety that has resulted from breeding and selection for superior horticultural performance for use in agriculture. This germplasm is easier to breed because it generally performs well when evaluated for horticultural performance. A number of cultivated melon types have been developed, which are agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. However, this approach generally presents significant difficulties due to fertility problems associated with crosses between diverse lines, and negative linkage drag from the non-cultivated parent. For example, non-cultivated melon lines can provide alleles associated with disease resistance. However, these non-cultivated lines may have poor horticultural qualities such as undesirable fruit shape, undesirable immature fruit color, small fruit size, or low yield.

In certain embodiments of the invention, ToLCNDV resistance alleles have been introgressed from the PI414723 *C. melo* ssp *agrestis* wild-type melon into commercial melon varieties, which are *C. melo* ssp *melo*. While crossing between melons of different subspecies is possible, the agronomic values of wild-type plants are very different from commercially acceptable melons. The potential for fertility problems or linkage drag is thus very high. In the absence of the novel genetic markers provided herein for accurately tracking resistance alleles during breeding, the production of commercially useful plants is highly unlikely.

Introgression of ToLCNDV resistance alleles to provide agronomically useful plants is further complicated because ToLCNDV resistance from PI414723 may be controlled by multiple genes, requiring the introgression of multiple QTLs to transfer the resistance to a different plant. Absent the identification of ToLCNDV resistance QTL, and markers for tracking these novel QTL, provided herein, there would be no expectation of success in introgressing more than one useful allele on different chromosomes into a new genetic background.

The process of introgressing desirable resistance genes from non-cultivated lines into elite cultivated lines while avoiding problems with linkage drag or low heritability of the desired trait in crosses with the non-cultivated lines is a long and often arduous process. Success in deploying alleles derived from wild relatives therefore strongly depends on minimal or truncated introgressions that lack detrimental effects and reliable marker assays that replace phenotypic screens. Success is further defined by simplifying genetics for key attributes to allow focus on genetic gain for quantitative traits such as disease resistance. Moreover, the process of introgressing genomic regions from non-cultivated lines can be greatly facilitated by the availability of accurate markers for marker-assisted selection (MAS).

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked using MAS. Thus, the novel, accurate markers associated with disease resistance provided herein will facilitate the development of melon plants having beneficial phenotypes. For example, seed can be genotyped using the markers of the present invention in order to select for plants comprising desired genomic regions associated with disease resistance, without the need for growing plants to maturity to evaluate the phenotype. Moreover, MAS allows identification of plants homozygous or heterozygous for a desired introgression.

Phenotypic evaluation of large plant populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among melon species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

Many desirable traits that are successfully introduced through introgression can also be introduced directly into a plant by the use of molecular techniques. One aspect of the invention includes plants with a genome that has been changed by any method using site-specific genome modification techniques. Techniques of site-specific genome modification include the use of enzymes such as, endonucleases, recombinases, transposases, helicases and any combination thereof. In one aspect, an endonuclease is selected from a meganuclease, a zinc-finger nuclease (ZFN), a transcription activator-like effector nucleases (TALEN), an Argonaute, and an RNA-guided nuclease, such as a CRISPR associated nuclease.

In another aspect, the endonuclease is a Cas9-recombinase fusion protein. As used herein, a "dCas9" refers to a Cas9 endonuclease protein with one or more amino acid mutations that result in a Cas9 protein without endonuclease activity, but retaining RNA-guided site-specific DNA binding. As used herein, a "dCas9-recombinase fusion protein" is a dCas9 with a protein fused to the dCas9 in such a manner that the recombinase is catalytically active on the DNA.

Non-limiting examples of recombinase include a tyrosine recombinase attached to a DNA recognition motif provided herein is selected from the group consisting of a Cre recombinase, a Gin recombinase a Flp recombinase, and a Tnp1 recombinase. In an aspect, a Cre recombinase or a Gin recombinase provided herein is tethered to a zinc-finger DNA-binding domain, or a TALE DNA-binding domain, or a Cas9 nuclease. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Site-specific genome modification enzymes, induce a genome modification such as a double-stranded DNA break (DSB) or single-strand DNA break at the target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of exogenous sequences by homologous recombination.

Another aspect of the invention includes transgenic plant cells, transgenic plant tissues, transgenic plants, and transgenic seeds that comprise the recombinant DNA molecules and engineered proteins provided by the invention. These cells, tissues, plants, and seeds comprising the recombinant DNA molecules and engineered proteins exhibit resistance to ToLCNDV. Suitable methods for transformation of host plant cells for use with the current invention include virtually any method by which DNA can be introduced into a cell (for example, where a recombinant DNA construct is stably integrated into a plant chromosome) and are well known in the art. An exemplary and widely utilized method for introducing a recombinant DNA construct into plants is the *Agrobacterium* transformation system, which is well known to those of skill in the art. Another exemplary method for introducing a recombinant DNA construct into plants is insertion of a recombinant DNA construct into a plant genome at a pre-determined site by methods of site-directed integration. Transgenic plants can be regenerated from a transformed plant cell by the methods of plant cell culture. A transgenic plant homozygous with respect to a transgene (that is, two allelic copies of the transgene) can be obtained by self-pollinating (selfing) a transgenic plant that contains a single transgene allele with itself, for example an R0 plant, to produce R1 seed. One fourth of the R1 seed produced will be homozygous with respect to the transgene. Plants grown from germinating R1 seed can be tested for zygosity, using a SNP assay, DNA sequencing, or a thermal amplification assay that allows for the distinction between heterozygotes and homozygotes, referred to as a zygosity assay.

IV. Molecular Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita et al. (1989) *Genomics,* 8(2), 271-278), denaturing gradient gel electrophoresis (Myers (1985) EPO 0273085), or cleavage fragment length polymorphisms (Life Technologies, Inc., Gathersberg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al. (1992) *Biotechniques* 12(1), 82-87), or PCR amplification of multiple specific alleles (PAMSA; Dutton and Sommer (1991) *Biotechniques,* 11(6), 700-7002).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a melon plant a genotype associated with disease resistance, identify a melon plant with a genotype associated with disease resistance, and to select a melon plant with a genotype associated with disease resistance. In certain embodiments of methods of the invention, polymorphic nucleic acids can be used to produce a melon plant that comprises in its genome an introgressed locus associated with disease resistance. In certain embodiments of the invention, polymorphic nucleic acids can be used to breed progeny melon plants comprising a locus or loci associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in melon plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201, 184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523 (2003); Cui et al., *Bioinformatics* 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

V. Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which melon plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "quantitative trait locus" (QTL) is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any variety that has resulted from breeding and selection for superior agronomic performance. An "elite plant" refers to a plant belonging to an elite variety. Numerous elite varieties are available and known to those of skill in the art of melon breeding. An "elite population" is an assortment of elite individuals or varieties that can be used to represent the state of the art in terms of agronomically superior genotypes of a given crop species, such as melon. Similarly, an "elite germplasm" or elite strain of germplasm is an agronomically superior germplasm.

As used herein, the term "introgressed" or "introgression," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked" or "genetically linked," when used in the context of nucleic acid markers and/or genomic regions, means that the markers and/or genomic regions are located in proximity on the same linkage group or chromosome such that they tend to segregate together at meiosis.

As used herein, "resistance locus" means a locus associated with resistance or tolerance to a disease. For instance, a resistance locus according to the present invention may, in one embodiment, control resistance or susceptibility to ToLCNDV.

As used herein, "resistance allele" means the nucleic acid sequence associated with resistance or tolerance to a disease.

As used herein, "resistance" or "improved resistance" in a plant to disease is an indication that the plant is more able to reduce disease damage than a non-resistant or less-resistant plant. One of skill will appreciate that plant resistance to disease varies widely, and can represent a spectrum of more-resistant or less-resistant phenotypes. However, by simple observation, one of skill can generally determine the relative resistance of different plants, plant varieties, or plant families to disease, and furthermore, will also recognize the phenotypic gradations of "resistance."

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

EXAMPLES

Example 1. Phenotyping ToLCNDV Resistance

A method of mechanical inoculation of cucurbitaceae, including melon plants, has been described (Lopez, et al. *Euphytica* (2015) 204:679-691). Three inoculum preparation methods are described, and the following inoculum preparation method resulted in the highest rate of infection: 1 g of infected zucchini leaves are ground with a mortar and pestle in 4 mL of inoculation buffer. Inoculation buffer comprises 50 mM potassium phosphate (pH 8.0), 1% polyvinylpyrrolidone 10, 1% polyethylene glycol 6000, 10 mM 2-mercaptoethanol, and 1% activated charcoal. This buffer is also known as the COMAV buffer. Freshly prepared inoculum should be kept on ice and discarded after 30 minutes. To inoculate, the two youngest fully expanded leaves of each plant are dusted with carborundum power 600 mesh. Subsequently, these leaves are gently rubbed with cotton buds soaked with the inoculum.

Alternatively, 2% (w/v) of carborundum can be added to the inoculation buffer. Subsequently, turgid leaves (which can be totally expanded cotyledons) are sprinkled with carborundum and then the inoculum is rubbed gently into the leaves between finger and thumb. It is important to not rub too hard and to regularly mix the inoculum. It is preferable to perform a second inoculation 2 days after the first to obtain optimal infection. Susceptible and resistant control varieties can be included in the experiment, and each genotype may be replicated at least twice within the experiment.

Plants should be grown in an environment with approximately 26° C. day/18° C. night temperatures and between 13 to 16 hours of daylight. In addition, the experimental environment should be kept free of whiteflies or aphids. Plants may be evaluated 15 and 28 days post infection (dpi) when all susceptible controls have symptoms. The plants described herein were scored using a 1 to 9 scale, where 1 is completely resistant (i.e. no symptoms) and 9 is completely susceptible (i.e. intense curling and bubbling of the leaves, mosaic and reduction of plant leaf size). Intermediate scores are determined in the following manner: 3=some yellow spots or light mosaic on the first leaves; 5=very mild curling, yellow spots and light mosaic on the leaves; 7=almost all leaves are affected by the virus and show curling, mild bubbling and mosaic.

Example 2. Whitefly Assay for ToLCNDV Resistance

An alternative method of testing for ToLCNDV resistance utilizes whiteflies (*Bemisia tabaci*) of biotype Q, which simulates natural infection. This method involves maintaining whitefly populations, which can be done for example in cages where whiteflies have access to aubergine plants. The whiteflies must be provided with healthy plants to keep them non-viruliferous. To prepare the whiteflies for an experiment involving ToLCNDV, non-viruliferous whiteflies of colonies that have been established for at least 6 weeks are exposed to ToLCNDV-infected melon plants (e.g. infected by mechanical inoculation) for 48 hours. To ensure optimal virus uptake by the whiteflies, the uninfected plants used for whitefly colony maintenance are replaced by infected plants in a cage.

An experimental design may include several control varieties, including a susceptible variety, an intermediate resistant variety, and a resistant variety (e.g. PI414723). It is important to include at least 3 susceptible controls and at least 2 resistant controls within each experimental tray. Each tested variety may have at least two or more replicates. Plants should be of similar developmental age and must have reached at least the first true leaf stage, and should not have been treated with pesticides. Experimental plants are inoculated by releasing ToLCNDV-exposed whiteflies (about 5 whiteflies are needed per plant) as described above among the plants that are to be tested for their ToLCNDV resistance. In certain examples, plants may be exposed to the whiteflies for approximately 72 hours, and may not be watered for the first 24 hours. Infection can be improved by disturbing the whiteflies every 24 to 36 hours by shaking the plants about 2 hours after watering. This will ensure a homogeneous distribution of the insects among the plants and improves infection. After 72 hours, the whiteflies may be killed using an adequate insecticide (e.g. imidacloprid). Plants may then be transplanted to a greenhouse where symptoms are evaluated 30, 45, and 60 days post inoculation (dpi) for an adult plant assay, or 21 and 28 dpi for a seedling assay. ToLCNDV resistance is scored on a 1 to 9 scale using the same scoring criteria as described for the mechanical inoculation assay in Example 1. An experiment is deemed successful if 90% of the susceptible checks have severe ToLCNDV symptoms (i.e. a score of 9). Experiments should be done during periods and climate conditions that correspond with natural whitefly presence (e.g. spring to early autumn). Optimal whitefly inoculation is achieved when day/night temperatures are 26° C./24° C.

Example 3. Mapping of ToLCNDV QTLs

One-hundred and twenty-four F5:6 families derived from the cross of Vedrantais (susceptible) with PI414723 (resistant) were screened for resistance to ToLCNDV using a whitefly inoculation assay. The whitefly inoculation assay was set up using a randomized complete block design with 3 replicates and 8 plants/family. Parents, $F_1$ plants, and pathology controls were included in each replicate. The seedlings were exposed to ToLCNDV-infected whiteflies for 48 hours, and then sprayed to remove the whiteflies and transplanted into a greenhouse. The trial was scored at 27, 42, and 60 dpi and ratings of 1, 3, 5, 7, and 9 were given. The phenotypic scores for the pathology controls and the parents were similar. The mapping population distribution was not normal, and heavily skewed to susceptible phenotypes. Area Under the Disease Progression Curve (AUDPC) was also calculated for each family.

Linkage mapping was done in JoinMap® (Kyazma, Netherlands) using fingerprint data of the $F_5$ generation. In the dataset, 712 markers were polymorphic and 29 markers and 11 individuals were excluded during quality control of the data. Parents were classified as follows for ahb format: Vedrantais (A) and PI414723 (B). The following mapping parameters were used: maximum likelihood mapping, 683 markers, 109 entries.

Sampling thresholds were changed to 0.1, 0.05, 0.01, 0.005, and 0.001. The resulting map consisted of 12 linkage groups. These were aligned to an internal consensus genetic map to determine chromosome and orientation. The alignment of the Vedrantais x PI414723 to the consensus map is very similar and initial QTL analysis was done with both maps. The Vedrantais x PI414723 linkage map was used for the final analysis due to better alignment of markers under QTLs on chromosomes 2 and 6.

Composite Interval Mapping (CIM) was conducted using WinQTLCartographer (North Carolina State University, Raleigh, N.C.). The dataset contained 115 $F_5$ parent genotypes and 91 $F_5$:$F_6$ families with phenotype information. All 12 chromosomes were tested at 1 cM intervals. Significant SNP markers identified by Forward and Backward Stepwise Regression were used as background markers with blocking windows of 10 cM for each background marker, and the test model at test sites within 10 cM excludes the corresponding background marker. A maximum of 7 background markers from the stepwise regression was allowed. Thresholds were obtained by 500 permutations for each trait (time point) with a false discovery rate (FDR) of 0.05. Selected markers developed for the mapping study are shown in Table 1.

The results for the two early time points (27 and 42 dpi) were very similar. Two major QTLs were identified on the distal end of chromosome 6 and on the proximal end of chromosome 11. Several minor QTL were also identified on chromosomes 2, and 12. The overall fraction of phenotypic variation explained by the two major QTLs was 33%. The results for the last time point (61 dpi) and AUDPC were very similar, but differed from the earlier time points in that the QTL on chromosome 11 has a much lower LOD and the QTLs on chromosome 2 and chromosome 12 were above the threshold line. With four QTLs, the overall fraction of phenotypic variation explained was 45%.

After initial QTL discovery, tissue from $F_5$ parents was genotyped using 37 Taqman markers across the intervals of interest (chromosome 2, chromosome 6, chromosome 11, and chromosome 12). One-hundred and thirty-three $F_5$ parents were genotyped, and 114 of these had phenotype information from the whitefly inoculation trial. Since many of the markers were not included in the Vedrantais x PI414723 linkage map, positions from the internal consensus map were used in the analysis. Composite interval mapping (CIM) was conducted using WinQTLCartographer. Chromosomes 6 and 12 were broken into two intervals to avoid large gaps between markers. A maximum of 5 background markers from the stepwise regression was allowed. Thresholds were obtained by 500 permutations for each trait (time point) with a false discovery rate (FDR) of 0.05.

The results for all time points (27, 42 and 61 dpi) and AUDPC were very similar. Two major QTLs were still present on the distal end of chromosome 6 and on the proximal end of chromosome 11. The minor QTL on chromosome 2 was over the threshold line and was considered significant. The overall fraction of phenotypic variation explained by the three QTLs was 44%, suggesting that the ToLCNDV resistance may also be influenced by environmental variation.

ToLCNDV. For the genotyping, additional markers were developed in the two QTL regions: Marker_29 within the QTL region on chromosome 6 and Marker_30, Marker_31, and Marker_32 within the QTL region on chromosome 11. The fine-mapping analysis did not conclusively reduce the interval on chromosome 6, although there is trend towards a 12 cM region between Marker_9 and Marker_29. The interval on chromosome 11 was reduced to a 5 cM region between Marker_30 and Marker_32.

TABLE 1

Markers for identifying ToLCNDV resistance loci in melon plants.

| Marker name | Chr | Public position (bp) | Public position SNP (bp) | Marker size (bp) | SNP position in marker (bp) | SNP change | Marker sequence (SEQ ID NO) | Fwd Primer (SEQ ID NO) | Rev Primer (SEQ ID NO) | Probe 1 (SEQ ID NO) | Probe 2 (SEQ ID NO) |
|---|---|---|---|---|---|---|---|---|---|---|---|
| Marker_1 | 2 | 572,594-573,112 | 573,028 | 521 | 445 | A/G | 1 | 2 | 3 | 4 | 5 |
| Marker_2 | 2 | 644,766-643,939 | 644,655 | 830 | 112 | A/C | 6 | 7 | 8 | 9 | 10 |
| Marker_3 | 2 | 801,814-800,954 | 801,778 | 917 | 251 | T/C | 11 | 12 | 13 | 14 | 15 |
| Marker_4 | 2 | 1,036,928-1,037,121 | 1,037,024 | 199 | 100 | T/G | 16 | 17 | 18 | 19 | 20 |
| Marker_5 | 2 | 1,582,236-1,581,578 | 1,581,938 | 658 | 298 | A/G | 21 | 22 | 23 | 24 | 25 |
| Marker_9 | 6 | 2,971,787-2,970,734 | 2,970,811 | 1057 | 977 | T/C | 26 | 27 | 28 | 29 | 30 |
| Marker_10 | 6 | 2,296,814-2,295,794 | 2,296,368 | 1021 | 447 | T/G | 31 | 32 | 33 | 34 | 35 |
| Marker_29 | 6 | 1,887,297-1,886,997 | 1,887,147 | 301 | 151 | C/T | 91 | 92 | 93 | 94 | 95 |
| Marker_11 | 6 | 1,500,128-1,500,007 | 1,500,067 | 121 | 61 | T/C | 36 | 37 | 38 | 39 | 40 |
| Marker_12 | 6 | 1,162,808-1,162,928 | 1,162,868 | 121 | 61 | C/G | 41 | 42 | 43 | 44 | 45 |
| Marker_13 | 6 | 874,505-874,266 | 874,401 | 240 | 105 | A/G | 46 | 47 | 48 | 49 | 50 |
| Marker_17 | 11 | 30,515,593-30,514,027 | 30,514,268 | 1562 | 1322 | A/G | 51 | 52 | 53 | 54 | 55 |
| Marker_30 | 11 | 30,131,432-30,131,713 | 30,131,582 | 301 | 151 | C/T | 96 | 97 | 98 | 99 | 100 |
| Marker_31 | 11 | 29,809,381-29,809,081 | 29,809,231 | 301 | 151 | A/C | 101 | 102 | 103 | 104 | 105 |
| Marker_18 | 11 | 29,786,185-29,787,304 | 29,787,219 | 1121 | 1036 | T/C | 56 | 57 | 58 | 59 | 60 |
| Marker_19 | 11 | 29,728,981-29,727,881 | 29,728,032 | 1154 | 950 | T/C | 61 | 62 | 63 | 64 | 65 |
| Marker_32 | 11 | 29,515,376-29,515,076 | 29,515,226 | 301 | 151 | A/G | 106 | 107 | 108 | 109 | 110 |
| Marker_20 | 11 | 29,073,045-29,074,326 | 29,073,324 | 1340 | 338 | A/G | 66 | 67 | 68 | 69 | 70 |
| Marker_21 | 11 | 28,434,127-28,435,301 | 28,434,168 | 1179 | 45 | A/T | 71 | 72 | 73 | 74 | 75 |
| Marker_25 | 12 | 3,541,296-3,542,371 | 3,541,677 | 1127 | 432 | T/C | 76 | 77 | 78 | 79 | 80 |
| Marker_26 | 12 | 15,324,646-15,323,132 | 15,323,352 | 1517 | 1294 | A/T | 81 | 82 | 83 | 84 | 85 |
| Marker_27 | 12 | 20,605,863-20,605,275 | 20,605,436 | 608 | 441 | A/C | 86 | 87 | 88 | 89 | 90 |

Example 4. ToLCNDV QTL Validation

Eleven $F_8$ families derived from a different cross of Vedrantais x PI414723 than the F5:6 population used for QTL mapping were screened for the presence of the 4 resistance QTLs. Because this population was developed initially for a different purpose, only plants with the QTL on chromosome 11, and plants with the QTLs on chromosome 2 and chromosome 11 were detected. These plants were screened for resistance to ToLCNDV using both the mechanical bioassay and the whitefly assay. From the mechanical assay, it was concluded that the presence of both the QTLs on chromosome 11 and chromosome 2 resulted in high resistance. Interestingly, the $F_8$ families with both QTLs that were resistant in the mechanical bioassay showed intermediate resistance when inoculated with whitefly.

Example 5. Fine Mapping of ToLCNDV QTLs

The QTLs on chromosome 6 and chromosome 11 were subsequently further fine mapped. For the fine mapping, additional lines were developed from a cross between a Galia susceptible line and PI414723. From the $BC_2$ offspring, plants were selected that had different recombination points across the QTL interval determined during the initial mapping. These selected lines were selfed to create $BC_2F2$ families. These families were planted and only those plants that were fixed for either recurrent parent or donor alleles were selected and selfed again. The resulting $BC_2F3$ plants were genotyped and phenotyped for their resistance against

Example 6. Validation of Resistance Conferred by ToLCNDV QTLs in Different Melon Varieties To study the effects of the identified ToLCNDV resistance loci in different genetic background, populations were developed in three different market melon types: Galia, Amarillo, and Italian. Galia is green fleshed round shaped melon with yellow/grayish, fully netted skin. Amarillo is a white fleshed melon with an oval shape and yellow skin with some ridges, but no netting. The Italian melon type is characterized by orange flesh and has a round shape with green skin that is netted and contains green ridges. Crosses were made between PI414723 and an elite non-resistant background from each market type. These lines were backcrossed to the recurrent parent (i.e. elite parent) and the $BC_1$ populations were genotyped for the loci on chromosome 6, 11, and 12. Selections were made for plants that had the different combinations of QTLs in such a way that all possible combinations were selected, including a line that had none of the introgressions. These plants were selfed to fix the ToLCNDV resistance genotype. The $BC_1F_2$ generation was genotyped again to ensure that the correct genotypes were fixed. The subsequent $BC_1F_3$ generation was tested for the level of ToLCNDV resistance using the whitefly inoculation method. Table 2 shows phenotypic data for different combinations of ToLCNDV resistance QTLs introduced into the Galia (GAL), Amarillo (AMA), and Italian (ITA) melon backgrounds. In Table 2, the numbers in the "QTL" column indicate the chromosomes with a ToLCNDV resistance introgression. The recurrent parent ("RP") and an offspring plant containing no ToLCNDV resistance introgressions ("none") function as the negative controls. The results show that the loci on chromosomes 11 and 12 alone have little effect on the resistance to ToLCNDV when inoculated with whiteflies. The locus on chromosome 6, however, provided increased resistance when present alone in all genetic backgrounds. Furthermore, a combination of the resistance loci on chromosome 6 and chromosome 11 provided an even higher level of resistance in all genetic backgrounds. The addition of the locus on chromosome 12 to the loci on both chromosomes 6 and 11 increased the resistance to ToLCNDV significantly in the Galia background, but not in the Amarillo and Italian melon backgrounds. A combination of resistance alleles on chromosomes 6 and 12 increased resistance significantly over the single QTLs in the Galia and Amarillo melon types, but only slightly in the Italian melon type. A combination of resistance loci on chromosome 11 and chromosome 12 did not significantly increase resistance in any of the melon types.

TABLE 2

Phenotypic data for single and combinations of ToLCNDV resistance QTLs in different melon type backgrounds (GAL: Galia; AMA: Amarillo; ITA: Italian).

| QTL | GAL | | AMA | | ITA | |
|---|---|---|---|---|---|---|
| Donor | 2.16 | E | 2.16 | F | 2.16 | E |
| 6, 11, 12 | 3.13 | E | 3.35 | DE | 3.68 | E |
| 6, 12 | 3.14 | DE | 2.4 | F | 4.89 | CD |
| 11, 12 | 3.72 | BCDE | 4.88 | B | 6.2 | BC |
| 6, 11 | 3.72 | CD | 2.29 | EF | 3.17 | E |
| 6 | 4.33 | ABC | 3.67 | CD | 5.3 | C |
| none | 4.39 | AB | 5.39 | AB | 7.72 | AB |
| RP | 4.55 | AB | 4.5 | BC | 7.23 | AB |
| 12 | 4.67 | AB | 4.61 | BC | 8.44 | A |
| 11 | 4.89 | A | 6.67 | A | 3.86 | DE |

The invention claimed is:

1. An elite *Cucumis melo* plant comprising a first introgressed allele at a Tomato leaf curl New Delhi virus (ToLCNDV) resistance locus on a first chromosome, wherein said first chromosome is chromosome 6, wherein said first introgressed allele confers to a plant increased resistance to Tomato leaf curl New Delhi virus (ToLCNDV) compared to a plant not comprising said allele, and wherein said locus comprises a marker selected from the group consisting of marker locus Marker_9 (SEQ ID NO: 26), marker locus Marker_10 (SEQ ID NO: 31), marker locus Marker_11 (SEQ ID NO: 36), marker locus Marker_12 (SEQ ID NO: 41), marker locus Marker_13 (SEQ ID NO: 46), and marker locus Marker_29 (SEQ ID NO: 91).

2. The *Cucumis melo* plant of claim 1, wherein said plant further comprises a second introgressed allele at a Tomato leaf curl New Delhi virus (ToLCNDV) resistance locus on a second chromosome selected from the group consisting of chromosomes 11, 2, and 12, wherein said second introgressed allele confers to a plant increased resistance to Tomato leaf curl New Delhi virus (ToLCNDV) compared to a plant not comprising said allele.

3. The *Cucumis melo* plant of claim 2, wherein said plant further comprises a third introgressed allele at a Tomato leaf curl New Delhi virus (ToLCNDV) resistance locus on a third chromosome selected from the group consisting of chromosomes 11, 2, and 12, wherein said third introgressed allele confers to a plant increased resistance to Tomato leaf curl New Delhi virus (ToLCNDV) compared to a plant not comprising said allele.

4. The *Cucumis melo* plant of claim 3, wherein said plant further comprises a fourth introgressed allele at a Tomato leaf curl New Delhi virus (ToLCNDV) resistance locus on a fourth chromosome selected from the group consisting of chromosomes 11, 2, and 12, wherein said fourth introgressed allele confers to a plant increased resistance to Tomato leaf curl New Delhi virus (ToLCNDV) compared to a plant not comprising said allele.

5. The *Cucumis melo* plant of claim 1, wherein said first introgressed allele is further defined as:

a) introgressed from a *Cucumis melo* ssp *agrestis* plant; or b) comprising the resistance haplotype of P1414723.

6. The *Cucumis melo* plant of claim 1, wherein said first introgressed allele is flanked in the genome of said plant by marker locus Marker_9 (SEQ ID NO: 26) and marker locus Marker_13 (SEQ ID NO: 46) on chromosome 6.

7. A plant part of the *Cucumis melo* plant of claim 1.

8. The plant part of claim 7, wherein said plant part is a cell, a seed, a root, a stem, a leaf, a fruit, a flower, or pollen.

9. A method of selecting a *Cucumis melo* plant exhibiting resistance ToLCNDV, comprising:

a) crossing the *Cucumis melo* plant of claim 1 with itself or with a second *Cucumis melo* plant of a different genotype to produce one or more progeny plants; and b) selecting a progeny plant comprising said first introgressed allele at said ToLCNDV resistance locus.

10. The method of claim 9, wherein selecting said progeny plant comprises identifying a genetic marker within or genetically linked to a genomic region between marker locus Marker_9 (SEQ ID NO: 26) and marker locus Marker_13 (SEQ ID NO:46) on chromosome 6.

11. The method of claim 10, wherein selecting a progeny plant further comprises detecting at least one polymorphism at a locus selected from the group consisting of marker locus Marker_9 (SEQ ID NO: 26), marker locus Marker_10 (SEQ ID NO: 31), marker locus Marker_29 (SEQ ID NO: 91), marker locus Marker_11 (SEQ ID NO: 36), and marker locus Marker_12 (SEQ ID NO: 41).

12. The method of claim 9, wherein a) said progeny plant is an $F_2$-$F_6$ progeny plant; or b) producing said progeny plant comprises backcrossing.

13. The method of claim 12, wherein backcrossing comprises from 2-7 generations of backcrossing.

14. A method of producing a *Cucumis melo* plant exhibiting resistance to ToLCNDV, comprising introgressing into a plant an allele at a ToLCNDV resistance locus, wherein said resistance locus is defined as located in a genomic region between:

a) marker locus Marker_1 (SEQ ID NO: 1) and marker locus Marker_5 (SEQ ID NO: 21) on chromosome 2;

b) marker locus Marker_9 (SEQ ID NO: 26) and marker locus Marker_13 (SEQ ID NO:46) on chromosome 6;

c) marker locus Marker_17 (SEQ ID NO: 51) and marker locus Marker_21 (SEQ ID NO: 71) on chromosome 11; or d) marker locus Marker_26 (SEQ ID NO: 81) and marker locus Marker_27 (SEQ ID NO: 86) on chromosome 12.

15. The method of claim 14, wherein said introgressing comprises:

a) backcrossing;

b) marker-assisted selection; or c) detecting at least one polymorphism at a locus selected from the group consisting of marker locus Marker_1 (SEQ ID NO: 1), marker locus Marker_2 (SEQ ID NO: 6), marker locus Marker_3 (SEQ ID NO: 11), marker locus Marker_4 (SEQ ID NO: 16), marker locus Marker_5 (SEQ ID NO: 21), marker locus Marker_9 (SEQ ID NO: 26), marker locus Marker_10 (SEQ ID NO: 31), marker locus Marker_11 (SEQ ID NO: 36), marker locus Marker_12 (SEQ ID NO: 41), marker locus Marker_13 (SEQ ID NO: 46), marker locus Marker_17 (SEQ ID NO: 51), marker locus Marker_18 (SEQ ID NO: 56), marker locus Marker_19 (SEQ ID NO: 61), marker locus Marker_20 (SEQ ID NO: 66), marker locus Marker_21 (SEQ ID NO: 71), marker locus Marker_29 (SEQ ID NO: 91), marker locus Marker_26 (SEQ ID NO: 81), marker locus Marker_30 (SEQ ID NO: 96), marker locus Marker_31 (SEQ ID NO: 101), marker locus Marker_32 (SEQ ID NO: 106) and marker locus Marker_27 (SEQ ID NO: 86).

16. A *Cucumis melo* plant obtainable by the method of claim 9.

17. A *Cucumis melo* plant obtainable by the method of claim 14.

18. The method of claim 10, wherein selecting a progeny plant further comprises identifying a genetic marker genetically linked to a second allele at a ToLCNDV resistance locus on a second chromosome selected from the group consisting of chromosomes 2, 11, and 12.

19. The method of claim 18, wherein selecting a progeny plant further comprises:

a) identifying a genetic marker within or genetically linked to a genomic region between marker locus Marker_1 (SEQ ID NO: 1) and marker locus Marker_5 (SEQ ID NO: 21) on chromosome 2;

b) identifying a genetic marker within or genetically linked to a genomic region between marker locus Marker_17 (SEQ ID NO: 51) and marker locus Marker_21 (SEQ ID NO: 71) on chromosome 11; or c) identifying a genetic marker within or genetically linked to a genomic region between marker locus Marker_25 (SEQ ID NO: 76) and marker locus Marker_27 (SEQ ID NO: 86) on chromosome 12.

20. The method of claim 19, wherein selecting a progeny plant further comprises further comprises detecting at least one polymorphism at a locus selected from the group consisting of marker locus Marker_1 (SEQ ID NO: 1), marker locus Marker_2 (SEQ ID NO: 6), marker locus Marker_3 (SEQ ID NO: 11), marker locus Marker_4 (SEQ ID NO: 16), marker locus Marker_5 (SEQ ID NO: 21), marker locus Marker_17 (SEQ ID NO: 51), marker locus Marker_18 (SEQ ID NO: 56), marker locus Marker_19 (SEQ ID NO: 61), marker locus Marker_20 (SEQ ID NO: 66), marker locus Marker_21 (SEQ ID NO: 71), marker locus Marker_25 (SEQ ID NO: 76), marker locus Marker_26 (SEQ ID NO: 81), marker locus Marker_27 (SEQ ID NO: 86), marker locus Marker_30 (SEQ ID NO: 96), marker locus Marker_31 (SEQ ID NO: 101), and marker locus Marker_32 (SEQ ID NO: 106).

* * * * *

SEQUENCE LISTING

```
<160> NUMBER OF SEQ ID NOS: 110

<210> SEQ ID NO 1
<211> LENGTH: 521
<212> TYPE: DNA
<213> ORGANISM: Cucumis melo
<220> FEATURE:
<221> NAME/KEY: misc_feature
<222> LOCATION: (508)..(508)
<223> OTHER INFORMATION: n is a, c, g, or t

<400> SEQUENCE: 1

acttcaatga agttgagtag caacgggttg gcgatggtgt cacaattctc gtcgatgttg      60

acagagttgc agattccagg gattagccga aggcgacttc tcgagattcc agttcttggg     120

cacgatgatt atcctgactg ggcgaatccc gggatgcgac gactcctagc tgcagggtca     180

agagtgaagc ccaatgtcgt ggttgctaag gatggaagtg gtcaattcag gaccattcaa     240

gcggctctcg accaagttcc aaagaggaag aacaatgcaa cttatgtgat tcatatcaag     300

gccggagtgt atcaggaata tctacaaatt aaaaagactg tcacccactt gatgctcatt     360

ggtgatggcc ccaaaaagac cattatcact ggaaacaaga actttgttga tggcacaccc     420

accttcaaaa cagcaaccgt tggtaagtgt ccttaaaatt tagttcttat ggtttgattc     480

aacgagaatt taaattattc acttgtcntt ttacacagga c                         521


<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2

gcacacccac cttcaaaaca g                                                21


<210> SEQ ID NO 3
<211> LENGTH: 35
<212> TYPE: DNA
<213> ORGANISM: Artificial Sequence
<220> FEATURE:
<223> OTHER INFORMATION: primer

<400> SEQUENCE: 3

caagtgaata atttaaattc tcgttgaatc aaacc                                 35
```

<210> SEQ ID NO 4
<211> LENGTH: 16
<212> TYPE: DNA
<213> ORGANISM: Artificial Sequence
<220> FEATURE:
<223> OTHER INFORMATION: probe

<400> SEQUENCE: 4
accgttggta agtgtc 16

<210> SEQ ID NO 5
<211> LENGTH: 15
<212> TYPE: DNA
<213> ORGANISM: Artificial Sequence
<220> FEATURE:
<223> OTHER INFORMATION: probe

<400> SEQUENCE: 5
ccgttggtga gtgtc 15

<210> SEQ ID NO 6
<211> LENGTH: 830
<212> TYPE: DNA
<213> ORGANISM: Cucumis melo

<400> SEQUENCE: 6
taataatcgc tgaagtgtaa ctcatttgtt atgcttcatc agcaagtgat tctttttctt 60
tgaaatgtat ggttttgcat tctccacacg gtaacattag aattgaacag aaatttcata 120
gcattggtcc gttgatatgt tttagaactg ggtttgattt ctttctcttc agaaatatat 180
tatttggatg ccaaattttg aaaagccaaa gcgaacttag ttcaatggta attgacatac 240
cgtttacact agaggttcga tccttcattc acacagttta ctaagataat atccaacaaa 300
ctaaaaccta tgttaaaaac agtttagtag cattttttta tgacttactc aaaaaatcta 360
acaaactaaa atatatgcta aaactttttc actgtagtct tctttcttat tcttcaggag 420
ttaggtgatt tgactcctct cttgctcttg ggacttggtt ggacaagttg tgagagcatg 480
gttataactc aaatcggatt ttatcaaact gtacttacat tatcagcact ttgttggttc 540
gccttggctt tagactcatc aagataattc tgataaatat aggaaacaaa tccccaaaga 600
gccaacacta aagccatagc cttcacccca ttcattttgt catggaaaaa tatcactgct 660
agaattggaa ccacaggcaa agccaatgtg ctgatcacat tagagaataa tgaagacact 720
tcaaaaatta accccaacaa accgacggaa gagacttgcc atgttactgc agtccaaacc 780
aatgtcataa aaataggaaa ctctcccttc ttcatatccc ctcatctcat 830

<210> SEQ ID NO 7
<211> LENGTH: 25
<212> TYPE: DNA
<213> ORGANISM: Artificial Sequence
<220> FEATURE:
<223> OTHER INFORMATION: primer

<400> SEQUENCE: 7
gcattctcca cacggtaaca ttaga 25

<210> SEQ ID NO 8
<211> LENGTH: 27
<212> TYPE: DNA
<213> ORGANISM: Artificial Sequence
<220> FEATURE:

<223> OTHER INFORMATION: primer

<400> SEQUENCE: 8
tctaaaacat atcaacggac caatgct 27

<210> SEQ ID NO 9
<211> LENGTH: 16
<212> TYPE: DNA
<213> ORGANISM: Artificial Sequence
<220> FEATURE:
<223> OTHER INFORMATION: probe

<400> SEQUENCE: 9
ttgaacagaa atttca 16

<210> SEQ ID NO 10
<211> LENGTH: 17
<212> TYPE: DNA
<213> ORGANISM: Artificial Sequence
<220> FEATURE:
<223> OTHER INFORMATION: probe

<400> SEQUENCE: 10
attgaacaga catttca 17

<210> SEQ ID NO 11
<211> LENGTH: 917
<212> TYPE: DNA
<213> ORGANISM: Cucumis melo
<220> FEATURE:
<221> NAME/KEY: misc_feature
<222> LOCATION: (1)..(55)
<223> OTHER INFORMATION: n is a, c, g, or t
<220> FEATURE:
<221> NAME/KEY: misc_feature
<222> LOCATION: (539)..(539)
<223> OTHER INFORMATION: n is a, c, g, or t

<400> SEQUENCE: 11
nnnnnnnnnn nnnnnnnnnn nnnnnnnnnn nnnnnnnnnn nnnnnnnnnn nnnnntcggt 60
tacttccctt ggaggaaaat tcggtttcct ttacttttct gcttcatatt ttgaagttgg 120
gatctgtaac gaagatcgac tccgaattgt taactaggat tgaaagtaga ttggccatga 180
tgttaaaaaa gtgtcatgcg tcagatttac ttgtcaaaaa ctatggagac gatgatggtg 240
tttacgatgt cgccgttgtt actcggatca taaaatctta tgcttctcac atatcagata 300
atgctcaatc aaatttatct gatgttggga gattggtgga tgattatctt atgcttgttg 360
cacaagatca gaacctcaaa gcagatggtt tcctagtcct cgcggaagca ttgccgcaag 420
atgctcgggt ttgttgtgac aatttgtata gagcaattga tatgtacctg aaggtaaaga 480
aagttccatt tggaaaatac taagtttcaa tttgaataat ctcaaattct tggtttggna 540
tcggttttga gcaatattaa cataattttt tgaaattttc caggcacatc ctgagttaac 600
agaagaagaa aggacatgcc tatgtagatc cttgaaatac cataaactat cccaagcagc 660
gaaggagcac ataatgaaga acaataggtt accgctgaaa tacgtaacaa gtttcattct 720
tttggaacaa gtgagcgtga caaagcctag aacatcattt ggatcggttg accgacaaat 780
gagaagccgg gttgtgctgg gtgaaagtaa atgtccagga acaagttgga cgttgaattc 840
acaaaacgag ataaatctga tgaaaaggga ggttgcgaca atgaaagggc agcttaatga 900
cattcagatg tgcaaga 917

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
gtcaaaaact atggagacga tgatggt 27

<210> SEQ ID NO 13
<211> LENGTH: 31
<212> TYPE: DNA
<213> ORGANISM: Artificial Sequence
<220> FEATURE:
<223> OTHER INFORMATION: primer

<400> SEQUENCE: 13
gagcattatc tgatatgtga gaagcataag a 31

<210> SEQ ID NO 14
<211> LENGTH: 13
<212> TYPE: DNA
<213> ORGANISM: Artificial Sequence
<220> FEATURE:
<223> OTHER INFORMATION: probe

<400> SEQUENCE: 14
aacggcaaca tcg 13

<210> SEQ ID NO 15
<211> LENGTH: 13
<212> TYPE: DNA
<213> ORGANISM: Artificial Sequence
<220> FEATURE:
<223> OTHER INFORMATION: probe

<400> SEQUENCE: 15
aacggcgaca tcg 13

<210> SEQ ID NO 16
<211> LENGTH: 199
<212> TYPE: DNA
<213> ORGANISM: Cucumis melo
<220> FEATURE:
<221> NAME/KEY: misc_feature
<222> LOCATION: (198)..(199)
<223> OTHER INFORMATION: n is a, c, g, or t

<400> SEQUENCE: 16
gtcctgaatg agaatcgttg aatatatcgg ttatcaatca tattcatcat agccataatc 60
ttgttcatgg ttgtatgttt cttccatatt ctcgtaatag agaccagaac catatgttcc 120
ataaccatca tcataatcgt catcctgctc ctctgtggtt tcaaattctt tagtagttgt 180
atttcgcggc ttgtcggnn 199

<210> SEQ ID NO 17
<211> LENGTH: 28
<212> TYPE: DNA
<213> ORGANISM: Artificial Sequence
<220> FEATURE:
<223> OTHER INFORMATION: primer

<400> SEQUENCE: 17
tcttgttcat ggttgtatgt ttcttcca 28

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
gcaggatgac gattatgatg atggt 25

<210> SEQ ID NO 19
<211> LENGTH: 19
<212> TYPE: DNA
<213> ORGANISM: Artificial Sequence
<220> FEATURE:
<223> OTHER INFORMATION: probe

<400> SEQUENCE: 19
tggttctggt ctatattac 19

<210> SEQ ID NO 20
<211> LENGTH: 19
<212> TYPE: DNA
<213> ORGANISM: Artificial Sequence
<220> FEATURE:
<223> OTHER INFORMATION: probe

<400> SEQUENCE: 20
tggttctggt ctctattac 19

<210> SEQ ID NO 21
<211> LENGTH: 658
<212> TYPE: DNA
<213> ORGANISM: Cucumis melo

<400> SEQUENCE: 21
taagacggga aagacgaggc cggtgatggc gaatgggaag caaaaagggt gtaagaaaat 60
attggttctt tatacaaatt tgggaagaat aggaagccag aaaagactaa ttgggtgatg 120
catcaatatc atttgggtca gcatgaggaa gagaaagaag gggagcttgt ggtttctaag 180
atattttatc aaacacagcc aaggcagtgc aattggtcgg agagaagttt ggccgctgcc 240
gagggaaatt tcgaggttgc aaatttgagt cgacgggaga cgagtgctgt gacgacaagg 300
agttgttctt ctatgactca ggctgacgac gtgtctccgg ccgccacaac cggtgttgga 360
tgttcaattt ctagctttag ttcgatggat attcaacatc tcaaatctga ccattttggg 420
tttgtcccat ttcgaacaac gtttgatgat caggttattc attttcacat caaaatcatt 480
tgaaaatatg cgtctactac tcatttgaaa ctaaatgatt ttggattctt aaaatagtta 540
catgctagct gattaatcaa gtagaacttt tttaaactga tcaatgaaaa tatatataaa 600
caatgaggca aataataaca ttagagacta actgttgatg aaattttgtg ttggtatc 658

<210> SEQ ID NO 22
<211> LENGTH: 17
<212> TYPE: DNA
<213> ORGANISM: Artificial Sequence
<220> FEATURE:
<223> OTHER INFORMATION: primer

<400> SEQUENCE: 22
cgggagacga gtgctgt 17

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
cgtcgtcagc ctgagtcata g 21

<210> SEQ ID NO 24
<211> LENGTH: 20
<212> TYPE: DNA
<213> ORGANISM: Artificial Sequence
<220> FEATURE:
<223> OTHER INFORMATION: probe

<400> SEQUENCE: 24
aagaacaact ccttgtcgtc 20

<210> SEQ ID NO 25
<211> LENGTH: 17
<212> TYPE: DNA
<213> ORGANISM: Artificial Sequence
<220> FEATURE:
<223> OTHER INFORMATION: probe

<400> SEQUENCE: 25
aacaactccc tgtcgtc 17

<210> SEQ ID NO 26
<211> LENGTH: 1057
<212> TYPE: DNA
<213> ORGANISM: Cucumis melo

<400> SEQUENCE: 26
caagttgaaa ataaaaggag gtcttacaac tttaggatta atatcatgtt tctttgataa 60
ggtacaaaag cttgtaaaac tcaaacgggt atttggttca gaaaagttag aatctatccc 120
aaagtaatga actcaaagag gcattatggg gagggatttt aagtctccat atttggggtt 180
taagtatctc taataagaac aaccattact tctcttattg tcaattggta attttgagcc 240
gaaattctat gtttctcctg tgattctatc catacaattc ttttaacaag gttctaatac 300
attgagaatc ctataatatg taggtttctg aataaggcag ctataagaag agtttcaaga 360
gatccacgga ggacatgcac agtgacagaa gtggaggaga caaaacaaat ggtgagaatg 420
ataccaatta tggcatgcac attcatacca agcgcaatgg tggcacaaac acacaccctt 480
tttatcaaac aaggcaccac tttgaataga agcattggta gccacttcaa agtccctcct 540
gctagtttat atgcttttgt taccatctcc atgcttctca ccattctcat ttatgacagg 600
taattgagta tcttcaaaac ttggttatga gtacatgaaa ttgagcactt gtcattgtct 660
aaactttgtt aataatgtca aaattcggat tagaaaatac acctgataat catgtgataa 720
tgatggtaaa tttttatcca cacacctgtg tggtacttgc cacataagtt gtgatgcgta 780
agttagaaag tatttctatg taaagagtta aaagtttcga gtataagaat gaacatactt 840
tctcttctca gctatcatga tgtatacttg acctagatct ttttctatag agtttttaga 900
gttgcattac gactatcttt tgattcacta ggttgaggca tgccacattt gatattttgt 960
tagggtcgac cggcctcggt tgaggttgaa tatgttggct tgggccaatt ccaacccaac 1020 cccctttct agccccatgc attttggtcc tcaggac 1057

<210> SEQ ID NO 27
<211> LENGTH: 23
<212> TYPE: DNA
<213> ORGANISM: Artificial Sequence
<220> FEATURE:
<223> OTHER INFORMATION: primer

<400> SEQUENCE: 27
gttgaggcat gccacatttg ata 23

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
ggcccaagcc aacatattca ac 22

<210> SEQ ID NO 29
<211> LENGTH: 15
<212> TYPE: DNA
<213> ORGANISM: Artificial Sequence
<220> FEATURE:
<223> OTHER INFORMATION: probe

<400> SEQUENCE: 29
ccggccttgg ttgag 15

<210> SEQ ID NO 30
<211> LENGTH: 14
<212> TYPE: DNA
<213> ORGANISM: Artificial Sequence
<220> FEATURE:
<223> OTHER INFORMATION: probe

<400> SEQUENCE: 30
cggcctcggt tgag 14

<210> SEQ ID NO 31
<211> LENGTH: 1021
<212> TYPE: DNA
<213> ORGANISM: Cucumis melo
<220> FEATURE:
<221> NAME/KEY: misc_feature
<222> LOCATION: (129)..(130)
<223> OTHER INFORMATION: n is a, c, g, or t
<220> FEATURE:
<221> NAME/KEY: misc_feature
<222> LOCATION: (133)..(135)
<223> OTHER INFORMATION: n is a, c, g, or t
<220> FEATURE:
<221> NAME/KEY: misc_feature
<222> LOCATION: (140)..(143)
<223> OTHER INFORMATION: n is a, c, g, or t
<220> FEATURE:
<221> NAME/KEY: misc_feature
<222> LOCATION: (145)..(146)
<223> OTHER INFORMATION: n is a, c, g, or t
<220> FEATURE:
<221> NAME/KEY: misc_feature
<222> LOCATION: (151)..(152)
<223> OTHER INFORMATION: n is a, c, g, or t
<220> FEATURE:
<221> NAME/KEY: misc_feature
<222> LOCATION: (156)..(157)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (161)..(163)
<223> OTHER INFORMATION: n is a, c, g, or t
<220> FEATURE:
<221> NAME/KEY: misc_feature
<222> LOCATION: (557)..(557)
<223> OTHER INFORMATION: n is a, c, g, or t
<220> FEATURE:
<221> NAME/KEY: misc_feature
<222> LOCATION: (561)..(562)
<223> OTHER INFORMATION: n is a, c, g, or t
<220> FEATURE:
<221> NAME/KEY: misc_feature
<222> LOCATION: (566)..(567)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (573)..(574)
<223> OTHER INFORMATION: n is a, c, g, or t
<220> FEATURE:
<221> NAME/KEY: misc_feature
<222> LOCATION: (576)..(585)
<223> OTHER INFORMATION: n is a, c, g, or t
<220> FEATURE:
<221> NAME/KEY: misc_feature
<222> LOCATION: (588)..(589)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (593)..(593)
<223> OTHER INFORMATION: n is a, c, g, or t
<220> FEATURE:
<221> NAME/KEY: misc_feature
<222> LOCATION: (596)..(608)
<223> OTHER INFORMATION: n is a, c, g, or t
<220> FEATURE:
<221> NAME/KEY: misc_feature
<222> LOCATION: (610)..(612)
<223> OTHER INFORMATION: n is a, c, g, or t
<220> FEATURE:
<221> NAME/KEY: misc_feature
<222> LOCATION: (614)..(618)
<223> OTHER INFORMATION: n is a, c, g, or t
<220> FEATURE:
<221> NAME/KEY: misc_feature
<222> LOCATION: (620)..(622)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (629)..(631)
<223> OTHER INFORMATION: n is a, c, g, or t
<220> FEATURE:
<221> NAME/KEY: misc_feature
<222> LOCATION: (633)..(634)
<223> OTHER INFORMATION: n is a, c, g, or t
<220> FEATURE:
<221> NAME/KEY: misc_feature
<222> LOCATION: (636)..(638)
<223> OTHER INFORMATION: n is a, c, g, or t
<220> FEATURE:

<221> NAME/KEY: misc_feature
<222> LOCATION: (641)..(644)
<223> OTHER INFORMATION: n is a, c, g, or t
<220> FEATURE:
<221> NAME/KEY: misc_feature
<222> LOCATION: (648)..(649)
<223> OTHER INFORMATION: n is a, c, g, or t
<220> FEATURE:
<221> NAME/KEY: misc_feature
<222> LOCATION: (653)..(655)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (659)..(664)
<223> OTHER INFORMATION: n is a, c, g, or t
<220> FEATURE:
<221> NAME/KEY: misc_feature
<222> LOCATION: (666)..(667)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (671)..(672)
<223> OTHER INFORMATION: n is a, c, g, or t
<220> FEATURE:
<221> NAME/KEY: misc_feature
<222> LOCATION: (674)..(675)
<223> OTHER INFORMATION: n is a, c, g, or t
<220> FEATURE:
<221> NAME/KEY: misc_feature
<222> LOCATION: (677)..(678)
<223> OTHER INFORMATION: n is a, c, g, or t
<220> FEATURE:
<221> NAME/KEY: misc_feature
<222> LOCATION: (680)..(681)
<223> OTHER INFORMATION: n is a, c, g, or t
<220> FEATURE:
<221> NAME/KEY: misc_feature
<222> LOCATION: (683)..(694)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (701)..(702)
<223> OTHER INFORMATION: n is a, c, g, or t
<220> FEATURE:
<221> NAME/KEY: misc_feature
<222> LOCATION: (704)..(705)
<223> OTHER INFORMATION: n is a, c, g, or t
<220> FEATURE:
<221> NAME/KEY: misc_feature
<222> LOCATION: (707)..(711)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (718)..(722)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t

```
<220> FEATURE:
<221> NAME/KEY: misc_feature
<222> LOCATION: (727)..(728)
<223> OTHER INFORMATION: n is a, c, g, or t
<220> FEATURE:
<221> NAME/KEY: misc_feature
<222> LOCATION: (730)..(733)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (740)..(741)
<223> OTHER INFORMATION: n is a, c, g, or t
<220> FEATURE:
<221> NAME/KEY: misc_feature
<222> LOCATION: (744)..(745)
<223> OTHER INFORMATION: n is a, c, g, or t
<220> FEATURE:
<221> NAME/KEY: misc_feature
<222> LOCATION: (750)..(754)
<223> OTHER INFORMATION: n is a, c, g, or t
<220> FEATURE:
<221> NAME/KEY: misc_feature
<222> LOCATION: (757)..(766)
<223> OTHER INFORMATION: n is a, c, g, or t
<220> FEATURE:
<221> NAME/KEY: misc_feature
<222> LOCATION: (769)..(772)
<223> OTHER INFORMATION: n is a, c, g, or t
<220> FEATURE:
<221> NAME/KEY: misc_feature
<222> LOCATION: (774)..(779)
<223> OTHER INFORMATION: n is a, c, g, or t
<220> FEATURE:
<221> NAME/KEY: misc_feature
<222> LOCATION: (781)..(786)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (791)..(793)
<223> OTHER INFORMATION: n is a, c, g, or t

<400> SEQUENCE: 31

cgaagaatgg ccactgttgc tactgcccgg aaattccatt agcagttcaa tttaaccgaa     60

gttttcatga cggagggaaa tttgattctc tttcgcacta ctgcggtgac ccaaatggaa    120

ggcctctann ttnnnttttn nnncnntttt nnaaanntna nnnattttga cctacaattt    180

tacaaaatta cccttttaca aaattttgct tagaccaaat aagcaggccc aaaaccctaa    240

atggatgtcc agcccaaatc caggcccata acaaaataag accatgccga ttgccgccac    300

tgctcatcgt tgaaaaaact ccggcgagac tctctgttgg tatcgtacca gcaaagctag    360

ccaagccatg accatgaggc gacgaggcga tgaactgata ctctacgaat gatgatgaag    420

tgaagtccgc tagcttcttc tgaagcgttc ttcattgcca gcattctaaa taccgaactg    480

agtttgagcc cgtgttggtt ctcagagtga gagtttagaa ctcttttacc ggtgaaactt    540

tgcgttgtac tctgtanttt nnaaaannant ttnngnnnnn nnnnnaannt ngnaannnnn    600

nnnnnnnngn nnannnnntn nntnaangnn ntnngnnntt nnnncccnna aannngnann    660

nnnntnncnt nntnnanncn ntnnnnnnnn nnnntngncc nnanngnnnn nggnaaannn    720

nnanttnntn nnngnccccn nttnnttttn nnnnttnnnn nnnnnnttnn nntnnnnnna    780

nnnnnnggna nnnttgtttc gtcttaatgg tggtgacttg ttctttcttg aagaccataa    840
```

```
ttgaatgctt gaagctctct tgtactggcg agttgcctcc caatgccagg tccggccaca    900

gcttcattca cgaccctaag gtccgtctgt ttttgcactt tctgttattt ttcagttctt    960

ttgatttggt aatgtcaacc tgatattggt tttggacaat gggtgagggg ttatcaaata   1020

t                                                                   1021


<210> SEQ ID NO 32
<211> LENGTH: 23
<212> TYPE: DNA
<213> ORGANISM: Artificial Sequence
<220> FEATURE:
<223> OTHER INFORMATION: primer

<400> SEQUENCE: 32

gatgaagtga agtccgctag ctt                                             23


<210> SEQ ID NO 33
<211> LENGTH: 25
<212> TYPE: DNA
<213> ORGANISM: Artificial Sequence
<220> FEATURE:
<223> OTHER INFORMATION: primer

<400> SEQUENCE: 33

gggctcaaac tcagttcggt attta                                           25


<210> SEQ ID NO 34
<211> LENGTH: 17
<212> TYPE: DNA
<213> ORGANISM: Artificial Sequence
<220> FEATURE:
<223> OTHER INFORMATION: probe

<400> SEQUENCE: 34

cttctgaagc tttcttc                                                    17


<210> SEQ ID NO 35
<211> LENGTH: 15
<212> TYPE: DNA
<213> ORGANISM: Artificial Sequence
<220> FEATURE:
<223> OTHER INFORMATION: probe

<400> SEQUENCE: 35

tctgaagcgt tcttc                                                      15


<210> SEQ ID NO 36
<211> LENGTH: 121
<212> TYPE: DNA
<213> ORGANISM: Cucumis melo

<400> SEQUENCE: 36

tttccttaaa caacacactg ccagaaaaat aataaaataa aaaactaacc cgaagtttat     60

cgattacttc ttgctgttct ttttcacgcc ttgaggtagc atccgaatgg cgtttcaatt    120

c                                                                    121


<210> SEQ ID NO 37
<211> LENGTH: 26
<212> TYPE: DNA
<213> ORGANISM: Artificial Sequence
<220> FEATURE:
<223> OTHER INFORMATION: primer

<400> SEQUENCE: 37
```

ccttaaacaa cacactgcca gaaaaa 26

<210> SEQ ID NO 38
<211> LENGTH: 21
<212> TYPE: DNA
<213> ORGANISM: Artificial Sequence
<220> FEATURE:
<223> OTHER INFORMATION: primer

<400> SEQUENCE: 38
tgctacctca aggcgtgaaa a 21

<210> SEQ ID NO 39
<211> LENGTH: 21
<212> TYPE: DNA
<213> ORGANISM: Artificial Sequence
<220> FEATURE:
<223> OTHER INFORMATION: probe

<400> SEQUENCE: 39
tgctacctca aggcgtgaaa a 21

<210> SEQ ID NO 40
<211> LENGTH: 18
<212> TYPE: DNA
<213> ORGANISM: Artificial Sequence
<220> FEATURE:
<223> OTHER INFORMATION: probe

<400> SEQUENCE: 40
ccgaagttta tcgattac 18

<210> SEQ ID NO 41
<211> LENGTH: 121
<212> TYPE: DNA
<213> ORGANISM: Cucumis melo

<400> SEQUENCE: 41
gctatggcga gaggcctcga ggattcaagt aacgaacaga atgaggactt gatttcagcc 60
cacatagtgg atctgtagtg aagaatcctc tgagccattt gctgaacttc aagctccagc 120
t 121

<210> SEQ ID NO 42
<211> LENGTH: 25
<212> TYPE: DNA
<213> ORGANISM: Artificial Sequence
<220> FEATURE:
<223> OTHER INFORMATION: primer

<400> SEQUENCE: 42
ctcgaggatt caagtaacga acaga 25

<210> SEQ ID NO 43
<211> LENGTH: 24
<212> TYPE: DNA
<213> ORGANISM: Artificial Sequence
<220> FEATURE:
<223> OTHER INFORMATION: primer

<400> SEQUENCE: 43
ggctcagagg attcttcact acag 24

<210> SEQ ID NO 44

<211> LENGTH: 18
<212> TYPE: DNA
<213> ORGANISM: Artificial Sequence
<220> FEATURE:
<223> OTHER INFORMATION: probe

<400> SEQUENCE: 44
atccactatg tgggctga 18

<210> SEQ ID NO 45
<211> LENGTH: 18
<212> TYPE: DNA
<213> ORGANISM: Artificial Sequence
<220> FEATURE:
<223> OTHER INFORMATION: probe

<400> SEQUENCE: 45
atccactatg tcggctga 18

<210> SEQ ID NO 46
<211> LENGTH: 240
<212> TYPE: DNA
<213> ORGANISM: Cucumis melo
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t

<400> SEQUENCE: 46
gtacagctga ggcctcaaat ttttcaattc ctgaatgaaa gatattatat aggtcaatgg 60
gatccacata cttttanaaa agatgaaact aagaaaatta aaaaatggag gtaaatatac 120
gcagacaaca aatttcagca cggaaattgg aaaaagcaaa gatctacagt agaagtaatc 180
atntntctct ctctctcaaa cccgatcatc ctgacagaga actaagattc tataaaatta 240

<210> SEQ ID NO 47
<211> LENGTH: 34
<212> TYPE: DNA
<213> ORGANISM: Artificial Sequence
<220> FEATURE:
<223> OTHER INFORMATION: primer

<400> SEQUENCE: 47
tgaaagatat tatataggtc aatgggatcc acat 34

<210> SEQ ID NO 48
<211> LENGTH: 24
<212> TYPE: DNA
<213> ORGANISM: Artificial Sequence
<220> FEATURE:
<223> OTHER INFORMATION: primer

<400> SEQUENCE: 48
gctttttcca atttccgtgc tgaa 24

<210> SEQ ID NO 49
<211> LENGTH: 24
<212> TYPE: DNA
<213> ORGANISM: Artificial Sequence
<220> FEATURE:
<223> OTHER INFORMATION: probe

<400> SEQUENCE: 49
cgtatattta cctccatttt ttaa 24

<210> SEQ ID NO 50
<211> LENGTH: 21
<212> TYPE: DNA
<213> ORGANISM: Artificial Sequence
<220> FEATURE:
<223> OTHER INFORMATION: probe

<400> SEQUENCE: 50
atatttacct ccacttttta a 21

<210> SEQ ID NO 51
<211> LENGTH: 1562
<212> TYPE: DNA
<213> ORGANISM: Cucumis melo
<220> FEATURE:
<221> NAME/KEY: misc_feature
<222> LOCATION: (93)..(93)
<223> OTHER INFORMATION: n is a, c, g, or t

<400> SEQUENCE: 51
aagcagataa tttcttgtta ttgagtcctc tagtctcgcc agaacttaaa actgatgact 60
tgtcctttga atcctcagct tgttcatggg agncaaaatt gtcagattca aagtcgtttg 120
atagatcctc cacagcaggt ctactttcag aagatccacc aggataggac gtgctatcct 180
caggtacatt gtcctccaca acttcattca catcaacaac acaggactta agtccttcca 240
cgggctcaga caccatttga gaagggctat tttccacagt atgttctggc tgagtttcat 300
cattcttctc ctcaacttgt ttatcctctt tcaataaatc agaagattcc acaatagaaa 360
tgttagagat ttccttcatt tcatttgatt tttcttcatg tatctcaact ctgagttcct 420
cagcaccagt tgtatcactc tgaggagcct tgacctgcaa catggcaata gtacctggtg 480
gggctacagc cacttctttg tatgaaggtg attttccaag gctaactatt gtattcttca 540
atgagctagc atcaattgga gttgaggatc taccaggttc tactacaaag ctgaccttgt 600
cagcagtttc agtggcagac accactgttg cagtttctgt agatgaggga attgacttaa 660
ccctgtaagt caaagttttg acaattctcc tcccaaattt ggaaccttga taggaattca 720
tagaatgatg atctgtataa ctaccatggg atattgttct tttctttaac acatataatc 780
gactgtttgg attattactc ttcagtttat gagcttcact ctcaacatct atattcatct 840
tctggtaact gaaaaccttg ccaaaagtgg ctcgacgttg cttcagccgc cgcccatatg 900
acccagctga tcttggacgt tgaactgatt gccatccatc ttctccttca gggtggagtt 960
cagatatgat atcatctaca gtttttggcc tttcctcagc agcttcctca gtaacaggct 1020
gcggggcttc aactggtgtc gtagtctcct cgtctgtact tggaccatcc cctggtacaa 1080
gtacaagtgt ctcttcatca gaaacctctt ttgagatctc ttggggagat tcttcactgt 1140
gtgccatgct tgcactatgg tcagatctcc cctttagctg caaggagaaa agaacaatga 1200
gatgaacaaa gcaacagtaa ggtttttcaa atgctgttta atcgatgtaa caaatgacct 1260
gtctttgttc gttaattaat ttttttcta actagggtca aagctttgtt ttcctatacc 1320
caagtaccca tggccacccc aagggttaga ctcaggaggc atcaaaggta ttgagtatta 1380
agctcactcg aaagtttaaa cttgggacct caaagccgat atgaccaaca gacctcaagc 1440

```
ccttgccaac aggccacacc ttggggcatc tactcattat taattataac ttaaaaacag   1500

ttattagtac ttcaattttt gtttcaaagg aaaaatatga tgttcaaaat aaaacaaata   1560

ta                                                                  1562


<210> SEQ ID NO 52
<211> LENGTH: 22
<212> TYPE: DNA
<213> ORGANISM: Artificial Sequence
<220> FEATURE:
<223> OTHER INFORMATION: primer

<400> SEQUENCE: 52

actagggtca aagctttgtt tt                                              22


<210> SEQ ID NO 53
<211> LENGTH: 24
<212> TYPE: DNA
<213> ORGANISM: Artificial Sequence
<220> FEATURE:
<223> OTHER INFORMATION: primer

<400> SEQUENCE: 53

ctttgatgcc tcctgagtct aacc                                            24


<210> SEQ ID NO 54
<211> LENGTH: 17
<212> TYPE: DNA
<213> ORGANISM: Artificial Sequence
<220> FEATURE:
<223> OTHER INFORMATION: probe

<400> SEQUENCE: 54

cctataccca agtaccc                                                    17


<210> SEQ ID NO 55
<211> LENGTH: 16
<212> TYPE: DNA
<213> ORGANISM: Artificial Sequence
<220> FEATURE:
<223> OTHER INFORMATION: probe

<400> SEQUENCE: 55

ctatacccga gtaccc                                                     16


<210> SEQ ID NO 56
<211> LENGTH: 1121
<212> TYPE: DNA
<213> ORGANISM: Cucumis melo

<400> SEQUENCE: 56

acatcactgc tggccgacag taattgatta ccaaagggta agaatcttgg acctgcacaa     60

aaaagttgta tgcactttgc attggttgat tattcgatag cgaaaacatc ggggagaagt    120

taaatggaat tcttggaagc aaggaaattc aattgaaaaa ggccagggag aagatgcttg    180

ctctggaaaa ccatgcctaa attgataata cgaaccttgg ttgccataga gaaatcttcc    240

tgcatttagt gtcatagttg ctggttgagg ctttcttcga cgtcggttgt gcccatcgag    300

acgtttccta caacttcgtt ttctatcatc aaactccgcc aaagaatgga atctacatca    360

acataagaaa ggaaccaaca gacaaaaata acaagtataa gaaacacaaa atgtaagtct    420

cacaaaggtt tgcatccaac acaaaaagac aaaaaaacag caccattttg aaatatatcc    480

atgagggaat gagaagatat ctatgattcc tatgttgatt gaataaataa gcgcgatttt    540
```

```
gtgaattgag tcgtgcaaat tgatccactc tatttatcat ttgtttccag ggtagtatga    600

gtaacaatac aagcacacct tatacatgtt actacagaaa aacaagtgca aatgcaaatg    660

caaattcaaa atggtagaaa agtgtaaaag aaaaaatatc cctctcacgt tctttagtac    720

gccttagaaa agaaatcgta tcaagcatac tacatatcat aagatcaata aaacttttca    780

ctaagagcat aatgcaaaac tccgagtcca aaatggtttt tataaattat agaaaatact    840

tagaaaatta aaaatatgga gaaagttgaa atggatggag ttttcaagtc aagatgatat    900

aggacaagat ggaaaaacaa caagcttaac cgcttaagta tatatccgat ctatataact    960

taaattctaa tgatcagaaa agaaaaccat ggaaattaat gtaaggcaga ataaatgaag   1020

caaattgcaa catatcgacg ttctaaacat tctaacccac ctgctacatt gctggcagaa   1080

tcgttgttcc tgaccgcaaa tggttacttt cggtgtttta g                       1121


<210> SEQ ID NO 57
<211> LENGTH: 30
<212> TYPE: DNA
<213> ORGANISM: Artificial Sequence
<220> FEATURE:
<223> OTHER INFORMATION: primer

<400> SEQUENCE: 57

gaaaaccatg gaaattaatg taaggcagaa                                      30


<210> SEQ ID NO 58
<211> LENGTH: 25
<212> TYPE: DNA
<213> ORGANISM: Artificial Sequence
<220> FEATURE:
<223> OTHER INFORMATION: primer

<400> SEQUENCE: 58

aatgtagcag gtgggttaga atgtt                                           25


<210> SEQ ID NO 59
<211> LENGTH: 20
<212> TYPE: DNA
<213> ORGANISM: Artificial Sequence
<220> FEATURE:
<223> OTHER INFORMATION: probe

<400> SEQUENCE: 59

attgcaacat attgacgttc                                                 20


<210> SEQ ID NO 60
<211> LENGTH: 18
<212> TYPE: DNA
<213> ORGANISM: Artificial Sequence
<220> FEATURE:
<223> OTHER INFORMATION: probe

<400> SEQUENCE: 60

tgcaacatat cgacgttc                                                   18


<210> SEQ ID NO 61
<211> LENGTH: 1154
<212> TYPE: DNA
<213> ORGANISM: Cucumis melo
<220> FEATURE:
<221> NAME/KEY: misc_feature
<222> LOCATION: (1102)..(1154)
<223> OTHER INFORMATION: n is a, c, g, or t
```

<400> SEQUENCE: 61

```
ctggttggag aatgcaaaag tcacattacc atgttggtat ttaattttgg ttgaccattt     60
gtgttgtaaa cgaatgcttc caaaattgga cttaaggtca tcctctcccg acggtagata    120
tcggcttctt ttagccaaaa gttattgaca caagctttag tccaaatcta tttacaagaa    180
gagaacttat ggtcattgtg ttgttatgtt gtttgtttaa agaatagagg tcttgcccat    240
tggtgaaaaa ttcaaagtga gaatggacca accggccttg aaatagacct agggattatg    300
cctttgaaat actatgggca tctaagctgt gataccactt tgagattgaa tatcccccaa    360
tgaagagatc acacaagatc ttgtgaattt gcttcaatca tataccattg ggtcttgctc    420
aaggtttagc aagggaaatg gttgtacaaa agtcattttg tcctttccaa acacacaaaa    480
ttattggaag ttgtgtcacg tgcatttaac atatcatgat ttgtattagg tgaccacttt    540
ggatttctaa gtatgtacaa gcgattaata ggaaaattgt attgggtggg gataaggaaa    600
acgtgaagga ataatactat ttttcaattt tctaacatag caaaaccttg gccacatctt    660
tcaggagttt attatcattg cacagctcca ctcgagcaca acctaacatc attaaaccga    720
cgaccatggg taatagattt cgggacctat ttatggtatt tctacaatga aaaacccaaa    780
agatgtgtct gattgtcatg aacataactt tggtacaaca ccacatacca tatctctatt    840
aatatgtatc acttccttta atgtcatctg taatccccct ttatagtagt gatgttacgt    900
gtctcgaaaa gccaaatatg cttcccctga tcagcacttg gtcgaagtgc gagtgattag    960
gtgtatatga agttgaggtc atgttgtcaa cattccattg cgaaaattcg aaatgaaaaa   1020
ctcttcctta agtgctttag ccttcattgc attatgtctt tagttgggca atcacctacg   1080
tgttggaaat accacaaata gnnnnnnnnn nnnnnnnnnn nnnnnnnnnn nnnnnnnnnn   1140
nnnnnnnnnn nnnn                                                     1154
```

<210> SEQ ID NO 62
<211> LENGTH: 19
<212> TYPE: DNA
<213> ORGANISM: Artificial Sequence
<220> FEATURE:
<223> OTHER INFORMATION: primer

<400> SEQUENCE: 62

```
cccctgatca gcacttggt                                                  19
```

<210> SEQ ID NO 63
<211> LENGTH: 29
<212> TYPE: DNA
<213> ORGANISM: Artificial Sequence
<220> FEATURE:
<223> OTHER INFORMATION: primer

<400> SEQUENCE: 63

```
ttgacaacat gacctcaact tcatataca                                       29
```

<210> SEQ ID NO 64
<211> LENGTH: 18
<212> TYPE: DNA
<213> ORGANISM: Artificial Sequence
<220> FEATURE:
<223> OTHER INFORMATION: probe

<400> SEQUENCE: 64

```
ctaatcactc acacttcg                                                   18
```

<210> SEQ ID NO 65
<211> LENGTH: 16
<212> TYPE: DNA
<213> ORGANISM: Artificial Sequence
<220> FEATURE:
<223> OTHER INFORMATION: probe

<400> SEQUENCE: 65
aatcactcgc acttcg 16

<210> SEQ ID NO 66
<211> LENGTH: 1340
<212> TYPE: DNA
<213> ORGANISM: Cucumis melo
<220> FEATURE:
<221> NAME/KEY: misc_feature
<222> LOCATION: (1)..(58)
<223> OTHER INFORMATION: n is a, c, g, or t

<400> SEQUENCE: 66
nnnnnnnnnn nnnnnnnnnn nnnnnnnnnn nnnnnnnnnn nnnnnnnnnn nnnnnnnncc 60
ctagttttcc ccaatagacg gaaatgggca accaacgact cattgtacca atcacttgca 120
gggaaatctc catcaacatg cccataacaa cgtgaaatct aaggaagtga ggccattcct 180
ttcgtcttac aactcctaga taggcaacaa aaaaatatgc tatcaagaac caacttggta 240
gtctcccaat ggctccgaga aagggatatg tcaagaattc aaagtcctcc aggaacgggt 300
gtaggtggta tgctgtttca ccatacatcc aagtttcatg aagcggcatt agatacggta 360
ggcatgctaa agtcctccac caccattttg gttttgtggt cattggaggg taacgataac 420
ttgtagggac atctttggat gcccgcggtg tcatgctaat atttttttc ccaggtaacc 480 ttgggatcgt acttagcaac ccacctagat ccccgcttaa gagaggggaa gatgcagcat 540
ttagctttaa gggtaagaga cctacattta aaaaattaat ggattacgaa atgaagcaca 600
ccattctttc tttgaatcaa ttactgaaaa ggaagatata attctttaag atgaaagcga 660
tacaaacgtc agacaagatt ttctttatat taatgttgcc actgcataat aattctttct 720
tcatatgaaa ctaggattat gttgaaataa gagggagatg agatatctcc aaaaccgcag 780
taaaacttgt ttcaatataa agatcaaata aaagatagat aaagattatg gaaggttttg 840
tatgcacctc catagtaaca tgtctgatgc tttaaatgag gttcccatga actcctaatg 900
ctagcagttt gtgtgctgca acgaggatta cgtaagatgg aagaacggct aggaatagat 960
aacttggaat ttgagaagaa gcacccagtg ggtgtggtgc atccattgag aatcatatct 1020
aagtttcctg tttaaagcca catcattgca gattgcagag tgtaagaaac aaagtcaatg 1080
gaaaacaaag gatacaatgc ctagttttaa aatttaaata ttttaatgat ttcttttta 1140 cataatttat ccataaaaat acatcaacgt taatattgaa aacattggct ttaatgaagt 1200
attagggatt gtggtagtta gaaaagtttt tatccgcaat tctcaaggac cattctcatt 1260
tagataactc tcttatctaa caaatggatc tactttcttg aacaatcttg aaaatggtca 1320
tacttcactc attattgagc 1340

<210> SEQ ID NO 67
<211> LENGTH: 24
<212> TYPE: DNA
<213> ORGANISM: Artificial Sequence
<220> FEATURE:
<223> OTHER INFORMATION: primer

<400> SEQUENCE: 67
ggtgtaggtg gtatgctgtt tcac 24

<210> SEQ ID NO 68
<211> LENGTH: 25
<212> TYPE: DNA
<213> ORGANISM: Artificial Sequence
<220> FEATURE:
<223> OTHER INFORMATION: primer

<400> SEQUENCE: 68
gactttagca tgcctaccgt atcta 25

<210> SEQ ID NO 69
<211> LENGTH: 15
<212> TYPE: DNA
<213> ORGANISM: Artificial Sequence
<220> FEATURE:
<223> OTHER INFORMATION: probe

<400> SEQUENCE: 69
ccgcttcatg aaact 15

<210> SEQ ID NO 70
<211> LENGTH: 14
<212> TYPE: DNA
<213> ORGANISM: Artificial Sequence
<220> FEATURE:
<223> OTHER INFORMATION: probe

<400> SEQUENCE: 70
cgcttcacga aact 14

<210> SEQ ID NO 71
<211> LENGTH: 1179
<212> TYPE: DNA
<213> ORGANISM: Cucumis melo
<220> FEATURE:
<221> NAME/KEY: misc_feature
<222> LOCATION: (270)..(270)
<223> OTHER INFORMATION: n is a, c, g, or t

<400> SEQUENCE: 71
gtcctgcaat tgaacccgag atgcgacctc ctaggtcagt atacaccgaa cctgtttatt 60
gtatgcctca cactaagctt tttactaact ctggacctgt tcctctagac ttggacttgg 120
agccaaagta acacgccatt tcagaaatgg accgtctaat gacccacttg atagaaaact 180
atatgccaaa ttagatgctg ggaaaaaaca agctgctaga aagatgtcgg aggagactcc 240
cgtacttgac aataaggatg acgacagcgn tgatgaagaa gaagagagta gaactgccat 300
cttcaataag aagcgagcag caaagccagt aaccatgcct cctttccagg ggaagaagaa 360
gcgaaggtaa cttttgcaga taggaatatt gattatctaa caggtcgtct ctgaaggtat 420
ttaattagtc cctaacaaag taccaaagaa gcgatgatat ctcgtcaata tctttttgta 480
gaatacaacc ttgaaatctt tgttgagatt gacttttcct agttatagag gtcgaattgt 540
tttaatatca aattataatg ttccaacttg aaagttatgt aaaattgcta tcctacattt 600
ttggtttaaa aggtaattta tccatatggt tgttaagccc tcattcttca atattggaag 660
attgttactc ttctgttctt cttgttggta gggaaatttc tcatccattt cccttgattt 720
tttccttgtt ttgataacac aattccttca acttctgtta catcgatgat atatgtctat 780
ttatatctat tgcagtttat taaaattttg tctaaatatt tttaacaatt ttgttactta 840
aaacaaaatt ttccaaaagt aattttcaat tatttaatat taaaattgat taaagcataa 900

```
atgacatatg aagtatattc ttttagagag gacatgggtt tattttatac atagagataa    960

caacattggt tacattatat aagccaaaaa gtcaattgtt atcttttatg aattgttcta   1020

aataaaaaca atcatatatt aatgtccatg accacccatt tgttttttct agtatacttt   1080

aaaattattt taacaatatt gttaatgaga tgctatacaa ttgcccatta acatcatgac   1140

aaactccaaa gtattaaaaa aattggattg aaaactaaa                          1179


<210> SEQ ID NO 72
<211> LENGTH: 19
<212> TYPE: DNA
<213> ORGANISM: Artificial Sequence
<220> FEATURE:
<223> OTHER INFORMATION: primer

<400> SEQUENCE: 72

cccgagatgc gacctccta                                                  19


<210> SEQ ID NO 73
<211> LENGTH: 28
<212> TYPE: DNA
<213> ORGANISM: Artificial Sequence
<220> FEATURE:
<223> OTHER INFORMATION: primer

<400> SEQUENCE: 73

agtaaaaagc ttagtgtgag gcatacaa                                        28


<210> SEQ ID NO 74
<211> LENGTH: 17
<212> TYPE: DNA
<213> ORGANISM: Artificial Sequence
<220> FEATURE:
<223> OTHER INFORMATION: probe

<400> SEQUENCE: 74

acaggttcgg tgtatac                                                    17


<210> SEQ ID NO 75
<211> LENGTH: 16
<212> TYPE: DNA
<213> ORGANISM: Artificial Sequence
<220> FEATURE:
<223> OTHER INFORMATION: probe

<400> SEQUENCE: 75

caggttcgga gtatac                                                     16


<210> SEQ ID NO 76
<211> LENGTH: 1127
<212> TYPE: DNA
<213> ORGANISM: Cucumis melo
<220> FEATURE:
<221> NAME/KEY: misc_feature
<222> LOCATION: (21)..(48)
<223> OTHER INFORMATION: n is a, c, g, or t
<220> FEATURE:
<221> NAME/KEY: misc_feature
<222> LOCATION: (640)..(662)
<223> OTHER INFORMATION: n is a, c, g, or t

<400> SEQUENCE: 76

ctgaatcagt aaaatcccaa nnnnnnnnnn nnnnnnnnnn nnnnnnnngg gtagatatat     60

tgataaccaa aatacaatgt tcacaaacga tccaaagaca agaaaagtaa gggaaataaa    120
```

```
gacaagtcca attccttcga gaaggctggc aacctctccc tctaaaagct tcagcagcca    180

ttacaaaata atacctacct gcaccaatcc ctaaaatctt cttcatatac ctcccattct    240

tagtgggttc catccggtat actcccttct cctattatct ctccccggtt tgtctcaagg    300

ttaaatacct tcttgccttt gcatttgtac atgtggacaa ttggggtcta atagaatatt    360

aactggggga ggaaatacca atgcaaggat ttgaacacag aacctcctaa accacactac    420

tctattacca tctaaaatcg ctgattggcc caaaagctta aactgatagg tgaaagctta    480

tttaaaataa tatctaacaa atttgatttt agaacatcaa aactaagaat gggtttaaac    540

actcaaaatc tcgtggaaac aatcagaaca atatgtacac agattaaggg tatcatccct    600

ttatctcgct actatttgtt caggcagact tgaacaccan nnnnnnnnnn nnnnnnnnnn    660

nnaaagtcta acagcctact aaccaacttc ttatccctta tttaatattt aagagccaag    720

cgtgctcaac aaattcaaga cagttttcta gtcacttcaa tttatttatt tgatttaaca    780

gagtttggtc agtgcttatc caattaaaac aagaacaact aatcaaattt gaagcaggaa    840

aaagaaataa actaaccctt caaccaacaa actgaacttt ttggcgtttc ttgctttgtc    900

tttttcctct ttgatgacgg cacgccctac agtttttata ccctgacatc cagaagtttg    960

ttatgtatct cctaaacgtt aaaagaaaaa aaacaaaaca aaacaaatct ttcgtctata   1020

ctggttaaaa atattagtat gctcaccttt acaacaactc caggaagcat gtttttaagg   1080

aagtgtagat taaaatgaag tttattccta tctgcatctt gaggaag                 1127
```

<210> SEQ ID NO 77
<211> LENGTH: 25
<212> TYPE: DNA
<213> ORGANISM: Artificial Sequence
<220> FEATURE:
<223> OTHER INFORMATION: primer

<400> SEQUENCE: 77
acacagaacc tcctaaacca cacta 25

<210> SEQ ID NO 78
<211> LENGTH: 25
<212> TYPE: DNA
<213> ORGANISM: Artificial Sequence
<220> FEATURE:
<223> OTHER INFORMATION: primer

<400> SEQUENCE: 78
cagtttaagc ttttgggcca atcag 25

<210> SEQ ID NO 79
<211> LENGTH: 20
<212> TYPE: DNA
<213> ORGANISM: Artificial Sequence
<220> FEATURE:
<223> OTHER INFORMATION: probe

<400> SEQUENCE: 79
ctctattacc atttaaaatc 20

<210> SEQ ID NO 80
<211> LENGTH: 18
<212> TYPE: DNA
<213> ORGANISM: Artificial Sequence
<220> FEATURE:
<223> OTHER INFORMATION: probe

<400> SEQUENCE: 80
ctattaccat ctaaaatc 18

<210> SEQ ID NO 81
<211> LENGTH: 1517
<212> TYPE: DNA
<213> ORGANISM: Cucumis melo

<400> SEQUENCE: 81
gatacactag taaaaaatgt aaagtcttag tagttaaaaa gacctaacca ataatgccta 60
gaccatagca ttaaacctaa aacctcctac aactcccctt tggacctatc gcctcctctc 120
aagtattccg taatttctct ctgagtatta tataattcct ctcaagccaa atcccgaaat 180
aatggcaaac aaacaagtct gcaagaggat tttgcccttc taccgaaaac ggcacattga 240
gcaaaacctc cttcctctga atcctgaaac ccctattgtg ccccagggaa actctagagg 300
tatccaagaa cttggaccaa attgactagc caatcataca cacccctaac taataaggag 360
gatgcttttg gtaaaagggt gcacatcagt tagtcagcac cagttttagg ctcaaattga 420
cccatcagct tgcagcagtc agagttcatt ggattggaaa ggttccgtaa taccgacaac 480
cattaataat aaaactgaga caaccaatgt ttttgtcggt ttaagtcttt ttttaatatt 540
ccatgttcac ccttagtctt ctgcacaaac tcgtattgat taactttctt gtgtaagacc 600
tggactttcc ccttttgaga tcttaacctt ccaaaacaaa gaaaatgaag aggtcgatag 660
ggggaagcaa gaaaaccctc aaaattcaga gagacccaga aaagaaagct ttgtgaagaa 720
caagggatca aaatatgaga atgtacgccc caatcaacat ggacacctct agaacagaag 780
gctacttcct atctctccgt ccacgagggg ggccccgtac caaaagtcag gacacaacat 840
aatataccgt acaaacaagg aaagagaagc aaaaacctca ccaaccacca ggaagaaaag 900
ggcagcccct taaggaaaag cacacggctc ctgagtaaca gtgtaactct aacacctatc 960
tagagatcac gtgttcaaac ctttaagtga gcttactacg aaattcattg atgtcttcca 1020
aatctaagcc tgaaggcaaa cgtaggtact cctagattag tggggaaggc cctattggat 1080
tattagggga aaaacccatt tgctaaacaa atcaataatt atgattcata taacactaaa 1140
acaatccaat tattaatcca gaacacagga acggaataag aaacaccaac agccagcaat 1200
tgagtgccac ctaatagacg agttgtaaaa tagagcagcc agactttggt accaaacgct 1260
tgcttcaaag aagtgaaatt cccgtaatag gggatatgct acttgaaaag cttgcatgag 1320
tccaatggac ataagctact tacatcttcc agcaaaaagt tcctttccaa acagactcac 1380
tccacaaatt tagcaacaaa agagttccag attaatcaat accaataggc aatgaattca 1440
acccactaca aatatgaaag gacagcaaat ttttcatata gtgtctggag cccttcttca 1500
acctgggctt gcaggac 1517

<210> SEQ ID NO 82
<211> LENGTH: 24
<212> TYPE: DNA
<213> ORGANISM: Artificial Sequence
<220> FEATURE:
<223> OTHER INFORMATION: primer

<400> SEQUENCE: 82
gtaccaaacg cttgcttcaa agaa 24

<210> SEQ ID NO 83
<211> LENGTH: 27
<212> TYPE: DNA

<213> ORGANISM: Artificial Sequence
<220> FEATURE:
<223> OTHER INFORMATION: primer

<400> SEQUENCE: 83
gtaagtagct tatgtccatt ggactca 27

<210> SEQ ID NO 84
<211> LENGTH: 21
<212> TYPE: DNA
<213> ORGANISM: Artificial Sequence
<220> FEATURE:
<223> OTHER INFORMATION: probe

<400> SEQUENCE: 84
ttttcaagta gcatatcccc t 21

<210> SEQ ID NO 85
<211> LENGTH: 18
<212> TYPE: DNA
<213> ORGANISM: Artificial Sequence
<220> FEATURE:
<223> OTHER INFORMATION: probe

<400> SEQUENCE: 85
tcaagtagca taacccct 18

<210> SEQ ID NO 86
<211> LENGTH: 608
<212> TYPE: DNA
<213> ORGANISM: Cucumis melo
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t
<220> FEATURE:
<221> NAME/KEY: misc_feature
<222> LOCATION: (455)..(456)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t

<400> SEQUENCE: 86
gaattatatt tatcaaaaga aaaccccttc cataaagcta atagttttgt cttcaatcta 60
ttaacatttc atttcaaatt ttggcaagtc aggaagtttc caacatattt acggtaaagg 120
aaaccaataa gttgataaat ataaactgaa agaataacaa tttcaaaagc tcattacagt 180
atcccaccag ttgttttttt ngatacagag ggagggtgac atcggtattg accagaccaa 240
actgttcttc atatgtttcc ttcaccaggg ctcaactccg ttggtgatac caaatgttat 300
agcaatgaca gcaagaactg actgagcaag caaaaataaa gcacaatttc aaaatcagta 360
gatggaaatc ataacatcct agcacaacac agtcaagtcc aagaaaatga aacatcaggc 420
aattaattga gaccattgaa attctnaaaa taatnncacc tgaaacttat aatctgagat 480
aatcaaactt acaaattttc ataagtcaat caactaagac tctacattac aaaaaatcat 540
ccatgcacta tgctttaatt ctcaaaagtg ggtcgatctc tttgtatggg ttaacaaaan 600
ctgtccga 608

<210> SEQ ID NO 87
<211> LENGTH: 26
<212> TYPE: DNA
<213> ORGANISM: Artificial Sequence
<220> FEATURE:
<223> OTHER INFORMATION: primer

<400> SEQUENCE: 87
cacaacacag tcaagtccaa gaaaat 26

<210> SEQ ID NO 88
<211> LENGTH: 37
<212> TYPE: DNA
<213> ORGANISM: Artificial Sequence
<220> FEATURE:
<223> OTHER INFORMATION: primer

<400> SEQUENCE: 88
tgtaagtttg attatctcag attataagtt tcaggtg 37

<210> SEQ ID NO 89
<211> LENGTH: 16
<212> TYPE: DNA
<213> ORGANISM: Artificial Sequence
<220> FEATURE:
<223> OTHER INFORMATION: probe

<400> SEQUENCE: 89
agaccattga aattct 16

<210> SEQ ID NO 90
<211> LENGTH: 16
<212> TYPE: DNA
<213> ORGANISM: Artificial Sequence
<220> FEATURE:
<223> OTHER INFORMATION: probe

<400> SEQUENCE: 90
agaccattga acttct 16

<210> SEQ ID NO 91
<211> LENGTH: 301
<212> TYPE: DNA
<213> ORGANISM: Cucumis melo
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (183)..(183)

<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (260)..(260)
<223> OTHER INFORMATION: n is a, c, g, or t

<400> SEQUENCE: 91
tgcantggac tcataaggtg aactcataaa gaagctttag gagcctagga aagagctcaa 60
gagagcaccc actaagtaga tanctccatg gaacatatga ggtaagcttc aagagaagtt 120
cnaatnagnt tnagcttagc ttaagagcag ccattcaaga catgtaagtt gataagagct 180
tanagagagc tcaagangag ctcaacgaga cctaggaaag nctagcctcn taagaccagg 240
aantnataag aggagaaccn actaggaaaa acccaatctt tctaatcata gtcgtaggag 300
g 301

<210> SEQ ID NO 92
<211> LENGTH: 25
<212> TYPE: DNA
<213> ORGANISM: Artificial sequence
<220> FEATURE:
<223> OTHER INFORMATION: Primer

<400> SEQUENCE: 92
ctccatggaa catatgaggt aagct 25

<210> SEQ ID NO 93
<211> LENGTH: 23
<212> TYPE: DNA
<213> ORGANISM: Artificial sequence
<220> FEATURE:
<223> OTHER INFORMATION: Primer

<400> SEQUENCE: 93
ctttcctagg tctcgttgag ctc 23

<210> SEQ ID NO 94
<211> LENGTH: 20
<212> TYPE: DNA
<213> ORGANISM: Artificial sequence
<220> FEATURE:
<223> OTHER INFORMATION: Probe

<400> SEQUENCE: 94
atgtcttgaa tggctgctct 20

<210> SEQ ID NO 95
<211> LENGTH: 19

```
<212> TYPE: DNA
<213> ORGANISM: Artificial sequence
<220> FEATURE:
<223> OTHER INFORMATION: Probe

<400> SEQUENCE: 95

tgtcttgaat gactgctct                                                19


<210> SEQ ID NO 96
<211> LENGTH: 301
<212> TYPE: DNA
<213> ORGANISM: Cucumis melo
<220> FEATURE:
<221> NAME/KEY: misc_feature
<222> LOCATION: (9)..(19)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t

<400> SEQUENCE: 96

tttatttgnn nnnnnnnnng cagtgcgctt ttctccgagc aatgctctat atggccattc     60

tgttgatact gttgcatctc actttgagga ggaggaagtt tttgagtcac ttgaagaatt    120

ggaggctcaa accatcggaa acctcctccc cgacgatgat gacttactgg cnggagtaac    180

tgatgggctn gattgtttgg ttgaaactac tggcgaggat gatgctgagg acttagattt    240

ttttagcaat gttggtggga tggatttggg tgatgatggt ttatctgtgg gacagaagaa    300

t                                                                    301


<210> SEQ ID NO 97
<211> LENGTH: 21
<212> TYPE: DNA
<213> ORGANISM: Artificial sequence
<220> FEATURE:
<223> OTHER INFORMATION: Primer

<400> SEQUENCE: 97

ggaggctcaa accatcggaa a                                              21


<210> SEQ ID NO 98
<211> LENGTH: 23
<212> TYPE: DNA
<213> ORGANISM: Artificial sequence
<220> FEATURE:
<223> OTHER INFORMATION: Primer

<400> SEQUENCE: 98

cctcgccagt agtttcaacc aaa                                            23


<210> SEQ ID NO 99
<211> LENGTH: 16
<212> TYPE: DNA
<213> ORGANISM: Artificial sequence
<220> FEATURE:
<223> OTHER INFORMATION: Probe

<400> SEQUENCE: 99

cctcctcccc gacgat                                                    16


<210> SEQ ID NO 100
```

<211> LENGTH: 16
<212> TYPE: DNA
<213> ORGANISM: Artificial sequence
<220> FEATURE:
<223> OTHER INFORMATION: Probe

<400> SEQUENCE: 100
cctcctccct gacgat 16

<210> SEQ ID NO 101
<211> LENGTH: 301
<212> TYPE: DNA
<213> ORGANISM: Cucumis melo
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t

<400> SEQUENCE: 101
gtcctaggct ggaaaattta caccattnag atctgaantg tgaatcttca aatgcatata 60
ttcacatacc ttttgcatat aactatgatt ttgcaggcaa ttccttctgg tccctccagg 120
caagttcttg aactccctcc aacaccttca acaaaggtaa attataagca ttcatctntt 180
taataacctt ttacagaaat tacatcagaa tggtgataga ttagataaag atattattgg 240
cttcgagggc tcattttaat tgttgcattc tctctgtttt tttttcagca gcaaaatcga 300
t 301

<210> SEQ ID NO 102
<211> LENGTH: 21
<212> TYPE: DNA
<213> ORGANISM: Artificial sequence
<220> FEATURE:
<223> OTHER INFORMATION: Primer

<400> SEQUENCE: 102
ccctccaggc aagttcttga a 21

<210> SEQ ID NO 103
<211> LENGTH: 31
<212> TYPE: DNA
<213> ORGANISM: Artificial sequence
<220> FEATURE:
<223> OTHER INFORMATION: Primer

<400> SEQUENCE: 103
tcaccattct gatgtaattt ctgtaaaagg t 31

<210> SEQ ID NO 104
<211> LENGTH: 17
<212> TYPE: DNA
<213> ORGANISM: Artificial sequence
<220> FEATURE:
<223> OTHER INFORMATION: Probe

<400> SEQUENCE: 104
caacaccttc aacaaag 17

<210> SEQ ID NO 105
<211> LENGTH: 17
<212> TYPE: DNA
<213> ORGANISM: Artificial sequence
<220> FEATURE:
<223> OTHER INFORMATION: Probe

<400> SEQUENCE: 105
caacaccttc accaaag 17

<210> SEQ ID NO 106
<211> LENGTH: 301
<212> TYPE: DNA
<213> ORGANISM: Cucumis melo
<220> FEATURE:
<221> NAME/KEY: misc_feature
<222> LOCATION: (251)..(251)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t

<400> SEQUENCE: 106
atctctagcc gttattagag cataagcacc aaataattaa catccagaga gttatataaa 60
gagtcaactt gcaacacacc cattacaata taatacctag tgcaggtcaa ctaggtattg 120
aattcatatt tgagttgaaa aggagagaga aaaaagtgtg tgtgatggga agtaatataa 180
tggggaatag aaacaaaaca ttgaatgaga gtatatattt gattatttga tcataagaga 240
tgtaagctaa nttcantcaa gagaagaaaa tatgttgatg tgatgtgatc attggtctct 300
a 301

<210> SEQ ID NO 107
<211> LENGTH: 27
<212> TYPE: DNA
<213> ORGANISM: Artificial sequence
<220> FEATURE:
<223> OTHER INFORMATION: Primer

<400> SEQUENCE: 107
tgcaggtcaa ctaggtattg aattcat 27

<210> SEQ ID NO 108
<211> LENGTH: 31
<212> TYPE: DNA
<213> ORGANISM: Artificial sequence
<220> FEATURE:
<223> OTHER INFORMATION: Primer

<400> SEQUENCE: 108
ctcattcaat gttttgtttc tattccccat t 31

<210> SEQ ID NO 109
<211> LENGTH: 19
<212> TYPE: DNA
<213> ORGANISM: Artificial sequence
<220> FEATURE:
<223> OTHER INFORMATION: Probe

<400> SEQUENCE: 109
acacacactt ttttctctc 19

<210> SEQ ID NO 110
<211> LENGTH: 18
<212> TYPE: DNA

-continued

```
<213> ORGANISM: Artificial sequence
<220> FEATURE:
<223> OTHER INFORMATION: Probe

<400> SEQUENCE: 110

cacacacttt tctctctc                                               18
```